United States Patent
Heo et al.

(10) Patent No.: US 11,111,485 B2
(45) Date of Patent: *Sep. 7, 2021

(54) EXPRESSION SYSTEM FOR PSICOSE EPIMERASE AND PRODUCTION FOR PSICOSE USING THE SAME

(71) Applicant: SAMYANG CORPORATION, Seoul (KR)

(72) Inventors: Jin Sol Heo, Incheon (KR); Hye Jung Kim, Daejeon (KR); Min Jeong Kim, Suwon-si (KR); Jeong Yoon Choi, Seoul (KR); Chong Jin Park, Daejeon (KR); Kang Pyo Lee, Seoul (KR)

(73) Assignee: SAMYANG CORPORATION, Seoul (KR)

( * ) Notice: Subject to any disclaimer, the term of this patent is extended or adjusted under 35 U.S.C. 154(b) by 273 days.

This patent is subject to a terminal disclaimer.

(21) Appl. No.: 16/274,654

(22) Filed: Feb. 13, 2019

(65) Prior Publication Data

US 2019/0169592 A1 Jun. 6, 2019

Related U.S. Application Data

(62) Division of application No. 14/927,731, filed on Oct. 30, 2015, now Pat. No. 10,240,140.

(30) Foreign Application Priority Data

Oct. 30, 2014 (KR) .................. 10-2014-0149019
May 22, 2015 (KR) .................. 10-2015-0072090

(51) Int. Cl.
*C12N 9/90* (2006.01)
*C12N 15/77* (2006.01)
*C12N 15/67* (2006.01)

(52) U.S. Cl.
CPC .............. *C12N 9/90* (2013.01); *C12N 15/67* (2013.01); *C12N 15/77* (2013.01); *C12Y 501/03* (2013.01)

(58) Field of Classification Search
None
See application file for complete search history.

(56) References Cited

U.S. PATENT DOCUMENTS

| | | |
|---|---|---|
| 2003/0104594 A1 | 6/2003 | Hallewell |
| 2008/0274516 A1 | 11/2008 | Kroger et al. |
| 2010/0068774 A1 | 3/2010 | Fukui |
| 2011/0104752 A1 | 5/2011 | Chevalet |
| 2014/0199732 A1 | 7/2014 | Kim et al. |

FOREIGN PATENT DOCUMENTS

| | | |
|---|---|---|
| JP | 2009-501547 | 1/2009 |
| JP | 2013-501519 | 1/2013 |
| KR | 10-2006-0068505 | 6/2006 |
| KR | 10-0620092 | 8/2006 |
| KR | 10-0744479 | 7/2007 |
| KR | 10-2011-0035805 | 4/2011 |
| KR | 10-1106253 | 1/2012 |
| KR | 10-2013-0064037 | 6/2013 |
| KR | 10-1318422 | 10/2013 |
| KR | 10-2013-0130377 | 12/2013 |
| KR | 10-2014-0021974 | 2/2014 |
| KR | 10-2014-0080282 | 6/2014 |
| KR | 10-1473918 | 12/2014 |
| KR | 10-1504900 | 3/2015 |
| WO | 2008/126896 | 10/2008 |
| WO | 2012/174271 | 12/2012 |

OTHER PUBLICATIONS

NCBI, GenBank Accession No. AY599234.1, 'Cloning and expression vector pUC18-mini-Tn7T-LAC, complete sequence', May 25, 2005.
NCBI, GenBank Accession No. JF828584.1, 'Expression vector lacl-ptac-gusA-pBAV1k, complete sequence', Jan. 2, 2012.
International Search Report, Patent Cooperation Treaty, dated Apr. 18, 2016, Application No. PCT/KR2015/011595.
Francois Baneyx, "Recombinant protein expression in *Escherichia coli*", Current Opinion Biotechnology, Oct. 1999, 10:411-421.
Park, Jong-Uk, et al., "Construction of Heat-Indudble Expression Vector of Corynebacterium glutamicum and C. ammoniagenes: Fusion of λ Operator with Promoters Isolated from C. ammoniagenes", J. Microbiol. Biotechnol., Apr. 2008, 18(4), 639-647.
Miroslav Pa'tek, et al., "Promoters of Corynebacterium glutamicum", Journal of Biotechnology 104, Sep. 2003, 311-323.
Meike Baumgart, et al., "Construction of a Prophage-Free Variant of Corynebacterium glutamicum ATCC 13032 for Use as a Platform Strain for Basic Research and Industrial Biotechnology", Applied and Environmental Microbiology, vol. 79, No. 19, Oct. 2013, pp. 6006-6015.
Dr Susan Carlson et al., "Original Submission 000001 Division of Biotechnology and GRAS Notice Review", Aug. 24, 2011, XP055167619, GRAS exemption claim for D-psicose, NutraSource, Inc.
EPO, A Supplementary European Search Report of EP 15853745.6 dated Mar. 6, 2018.
Xiaobo Li et al., "Overexpression of D-psicose 3-epimerase from Clostridium cellulolyticum H10 in Bacillus subtilis and its Prospect for D-psicose Production", Advance Journal of Food Science and Technology 5(3): 264-269, 2013.

*Primary Examiner* — Suzanne M Noakes
(74) *Attorney, Agent, or Firm* — Lex IP Meister, PLLC

(57) ABSTRACT

A gene expression cassette capable of producing psicose at high yield with high stability, a GRAS (Generally recognized as safe) microorganism, a method of producing the enzyme by using the GRAS microorganism, and a method of producing the psicose by using the GRAS microorganism and enzyme are provided.

16 Claims, 2 Drawing Sheets
(2 of 2 Drawing Sheet(s) Filed in Color)
Specification includes a Sequence Listing.

[FIG. 1]
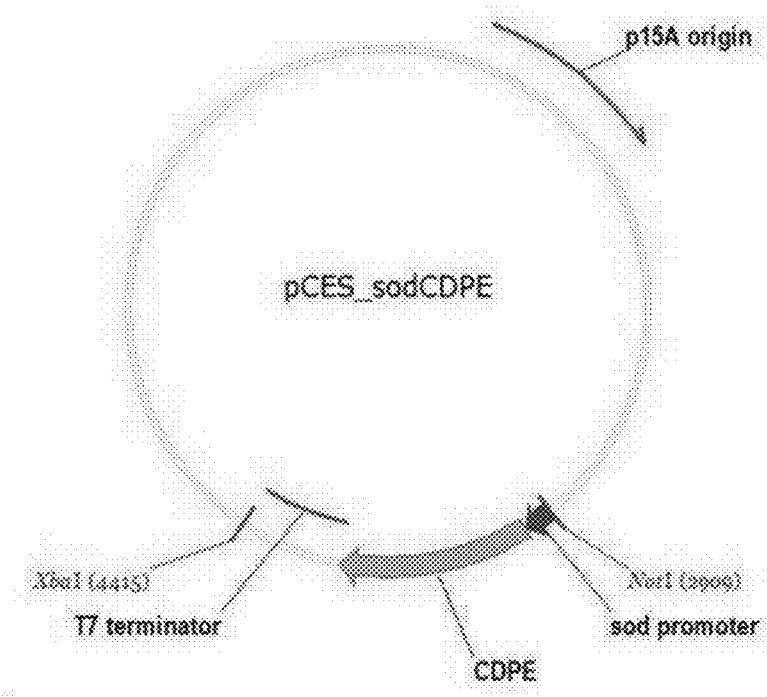

[FIG. 2]
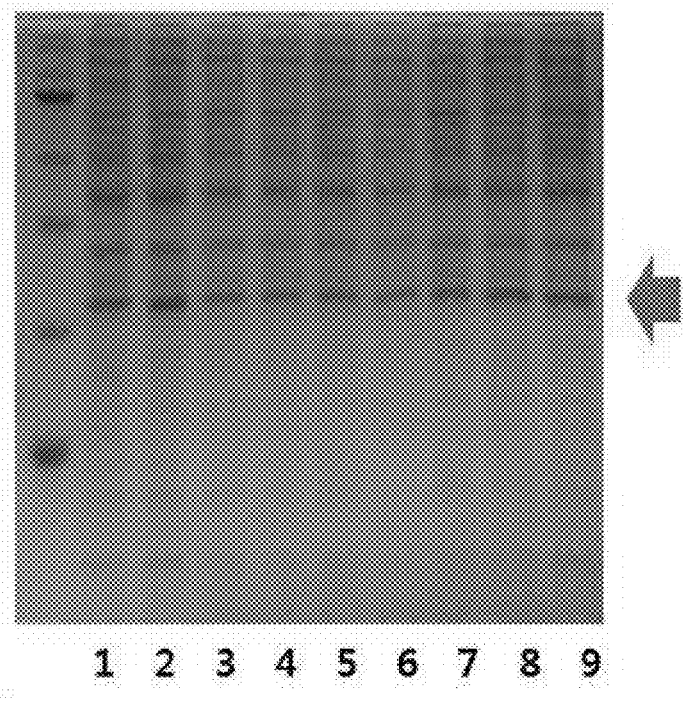
Lane 1 control (sodCDPE)
Lane 2 R1GA
Lane 3 R1GT
Lane 4 R1GC
Lane 5 R1GG
Lane 6 R1GA/R2GA
Lane 7 R1GA/R1GT
Lane 8 R1GA/R1GC
Lane 9 R1GA/R1GG

SEQUENCE LISTING

<160> NUMBER OF SEQ ID NOS: 62

<210> SEQ ID NO 1
<211> LENGTH: 283
<212> TYPE: DNA
<213> ORGANISM: Artificial Sequence
<220> FEATURE:
<223> OTHER INFORMATION: promotor -continued

<400> SEQUENCE: 1

```
aagcgcctca tcagcggtaa ccatcacggg ttcgggtgcg aaaaaccatg ccataacagg    60
aatgttcctt tcgaaaattg aggaagcctt atgcccttca accctactta gctgccaatt   120
attccgggct tgtgacccgc tacccgataa ataggtcggc tgaaaaattt cgttgcaata   180
tcaacaaaaa ggcctatcat tgggaggtgt cgcaccaagt acttttgcga agcgccatct   240
gacggatttt caaagatgt atatgctcgg tgcggaaacc tac                      283
```

<210> SEQ ID NO 2
<211> LENGTH: 7
<212> TYPE: DNA
<213> ORGANISM: Artificial Sequence
<220> FEATURE:
<223> OTHER INFORMATION: RBS

<400> SEQUENCE: 2

```
gaaagga                                                               7
```

<210> SEQ ID NO 3
<211> LENGTH: 10
<212> TYPE: DNA
<213> ORGANISM: Artificial Sequence
<220> FEATURE:
<223> OTHER INFORMATION: 1ST SPACER R1TT

<400> SEQUENCE: 3

```
tttttacccc                                                           10
```

<210> SEQ ID NO 4
<211> LENGTH: 10
<212> TYPE: DNA
<213> ORGANISM: Artificial Sequence
<220> FEATURE:
<223> OTHER INFORMATION: 1ST SPACER R1GA

<400> SEQUENCE: 4

```
gattttaccc                                                           10
```

<210> SEQ ID NO 5
<211> LENGTH: 10
<212> TYPE: DNA
<213> ORGANISM: Artificial Sequence
<220> FEATURE:
<223> OTHER INFORMATION: 1ST SPACER R1GT

<400> SEQUENCE: 5

```
gtttttaccc                                                           10
```

<210> SEQ ID NO 6
<211> LENGTH: 10
<212> TYPE: DNA
<213> ORGANISM: Artificial Sequence
<220> FEATURE:
<223> OTHER INFORMATION: 1ST SPACER R1GC

<400> SEQUENCE: 6

```
gcttttaccc                                                           10
```

<210> SEQ ID NO 7
<211> LENGTH: 7
<212> TYPE: DNA
<213> ORGANISM: Artificial Sequence
<220> FEATURE:
<223> OTHER INFORMATION: 2nd SPACER R2TT

<400> SEQUENCE: 7 ttacaaa                                                                    7

<210> SEQ ID NO 8
<211> LENGTH: 7
<212> TYPE: DNA
<213> ORGANISM: Artificial Sequence
<220> FEATURE:
<223> OTHER INFORMATION: 2nd SPACER R2GA

<400> SEQUENCE: 8 gaacaaa                                                                    7

<210> SEQ ID NO 9
<211> LENGTH: 7
<212> TYPE: DNA
<213> ORGANISM: Artificial Sequence
<220> FEATURE:
<223> OTHER INFORMATION: 2nd SPACER R2GT

<400> SEQUENCE: 9 gtacaaa                                                                    7

<210> SEQ ID NO 10
<211> LENGTH: 7
<212> TYPE: DNA
<213> ORGANISM: Artificial Sequence
<220> FEATURE:
<223> OTHER INFORMATION: 2nd SPACER R2GC

<400> SEQUENCE: 10 gcacaaa                                                                    7

<210> SEQ ID NO 11
<211> LENGTH: 7
<212> TYPE: DNA
<213> ORGANISM: Artificial Sequence
<220> FEATURE:
<223> OTHER INFORMATION: 2nd SPACER R2GG

<400> SEQUENCE: 11 ggacaaa                                                                    7

<210> SEQ ID NO 12
<211> LENGTH: 42
<212> TYPE: DNA
<213> ORGANISM: Artificial Sequence
<220> FEATURE:
<223> OTHER INFORMATION: Linker

<400> SEQUENCE: 12
atggctgtat acgaactccc agaactcgac tacgcatacg ac                             42

<210> SEQ ID NO 13
<211> LENGTH: 300
<212> TYPE: DNA
<213> ORGANISM: Artificial Sequence
<220> FEATURE:
<223> OTHER INFORMATION: RBS1/1st SPACER-TT

<400> SEQUENCE: 13
aagcgcctca tcagcggtaa ccatcacggg ttcgggtgcg aaaaaccatg ccataacagg          60
aatgttcctt tcgaaaattg aggaagcctt atgcccttca accctactta gctgccaatt        120

```
attccgggct tgtgacccgc tacccgataa ataggtcggc tgaaaatttt cgttgcaata    180
tcaacaaaaa ggcctatcat tgggaggtgt cgcaccaagt acttttgcga agcgccatct    240
gacggatttt caaaagatgt atatgctcgg tgcggaaacc tacgaaagga tttttttaccc   300
```

<210> SEQ ID NO 14
<211> LENGTH: 300
<212> TYPE: DNA
<213> ORGANISM: Artificial Sequence
<220> FEATURE:
<223> OTHER INFORMATION: RBS1/1st SPACER-GA

<400> SEQUENCE: 14

```
aagcgcctca tcagcggtaa ccatcacggg ttcgggtgcg aaaaaccatg ccataacagg     60
aatgttcctt tcgaaaattg aggaagcctt atgcccttca accctactta gctgccaatt    120
attccgggct tgtgacccgc tacccgataa ataggtcggc tgaaaatttt cgttgcaata    180
tcaacaaaaa ggcctatcat tgggaggtgt cgcaccaagt acttttgcga agcgccatct    240
gacggatttt caaaagatgt atatgctcgg tgcggaaacc tacgaaagga gatttttaccc   300
```

<210> SEQ ID NO 15
<211> LENGTH: 300
<212> TYPE: DNA
<213> ORGANISM: Artificial Sequence
<220> FEATURE:
<223> OTHER INFORMATION: RBS1/1st SPACER-GT

<400> SEQUENCE: 15

```
aagcgcctca tcagcggtaa ccatcacggg ttcgggtgcg aaaaaccatg ccataacagg     60
aatgttcctt tcgaaaattg aggaagcctt atgcccttca accctactta gctgccaatt    120
attccgggct tgtgacccgc tacccgataa ataggtcggc tgaaaatttt cgttgcaata    180
tcaacaaaaa ggcctatcat tgggaggtgt cgcaccaagt acttttgcga agcgccatct    240
gacggatttt caaaagatgt atatgctcgg tgcggaaacc tacgaaagga gtttttaccc    300
```

<210> SEQ ID NO 16
<211> LENGTH: 300
<212> TYPE: DNA
<213> ORGANISM: Artificial Sequence
<220> FEATURE:
<223> OTHER INFORMATION: RBS1/1st SPACER-GC

<400> SEQUENCE: 16

```
aagcgcctca tcagcggtaa ccatcacggg ttcgggtgcg aaaaaccatg ccataacagg     60
aatgttcctt tcgaaaattg aggaagcctt atgcccttca accctactta gctgccaatt    120
attccgggct tgtgacccgc tacccgataa ataggtcggc tgaaaatttt cgttgcaata    180
tcaacaaaaa ggcctatcat tgggaggtgt cgcaccaagt acttttgcga agcgccatct    240
gacggatttt caaaagatgt atatgctcgg tgcggaaacc tacgaaagga gctttttaccc   300
```

<210> SEQ ID NO 17
<211> LENGTH: 342
<212> TYPE: DNA
<213> ORGANISM: Artificial Sequence
<220> FEATURE:
<223> OTHER INFORMATION: RBS1/1st SPACER-TT/linker

<400> SEQUENCE: 17

```
aagcgcctca tcagcggtaa ccatcacggg ttcgggtgcg aaaaaccatg ccataacagg     60
aatgttcctt tcgaaaattg aggaagcctt atgcccttca accctactta gctgccaatt    120
```

```
attccgggct tgtgacccgc tacccgataa ataggtcggc tgaaaaattt cgttgcaata    180
tcaacaaaaa ggcctatcat tgggaggtgt cgcaccaagt acttttgcga agcgccatct    240
gacggatttt caaaagatgt atatgctcgg tgcggaaacc tacgaaagga ttttttaccc    300
atggctgtat acgaactccc agaactcgac tacgcatacg ac                      342
```

<210> SEQ ID NO 18
<211> LENGTH: 356
<212> TYPE: DNA
<213> ORGANISM: Artificial Sequence
<220> FEATURE:
<223> OTHER INFORMATION: R1GA/R2TT

<400> SEQUENCE: 18

```
aagcgcctca tcagcggtaa ccatcacggg ttcgggtgcg aaaaaccatg ccataacagg     60
aatgttcctt tcgaaaattg aggaagcctt atgcccttca accctactta gctgccaatt    120
attccgggct tgtgacccgc tacccgataa ataggtcggc tgaaaaattt cgttgcaata    180
tcaacaaaaa ggcctatcat tgggaggtgt cgcaccaagt acttttgcga agcgccatct    240
gacggatttt caaaagatgt atatgctcgg tgcggaaacc tacgaaagga gattttaccc    300
atggctgtat acgaactccc agaactcgac tacgcatacg acgaaaggat tacaaa       356
```

<210> SEQ ID NO 19
<211> LENGTH: 356
<212> TYPE: DNA
<213> ORGANISM: Artificial Sequence
<220> FEATURE:
<223> OTHER INFORMATION: R1GA/R2GA

<400> SEQUENCE: 19

```
aagcgcctca tcagcggtaa ccatcacggg ttcgggtgcg aaaaaccatg ccataacagg     60
aatgttcctt tcgaaaattg aggaagcctt atgcccttca accctactta gctgccaatt    120
attccgggct tgtgacccgc tacccgataa ataggtcggc tgaaaaattt cgttgcaata    180
tcaacaaaaa ggcctatcat tgggaggtgt cgcaccaagt acttttgcga agcgccatct    240
gacggatttt caaaagatgt atatgctcgg tgcggaaacc tacgaaagga gattttaccc    300
atggctgtat acgaactccc agaactcgac tacgcatacg acgaaaggag aacaaa       356
```

<210> SEQ ID NO 20
<211> LENGTH: 356
<212> TYPE: DNA
<213> ORGANISM: Artificial Sequence
<220> FEATURE:
<223> OTHER INFORMATION: R1GA/R2GT

<400> SEQUENCE: 20

```
aagcgcctca tcagcggtaa ccatcacggg ttcgggtgcg aaaaaccatg ccataacagg     60
aatgttcctt tcgaaaattg aggaagcctt atgcccttca accctactta gctgccaatt    120
attccgggct tgtgacccgc tacccgataa ataggtcggc tgaaaaattt cgttgcaata    180
tcaacaaaaa ggcctatcat tgggaggtgt cgcaccaagt acttttgcga agcgccatct    240
gacggatttt caaaagatgt atatgctcgg tgcggaaacc tacgaaagga gattttaccc    300
atggctgtat acgaactccc agaactcgac tacgcatacg acgaaaggag tacaaa       356
```

<210> SEQ ID NO 21
<211> LENGTH: 356
<212> TYPE: DNA

```
<213> ORGANISM: Artificial Sequence
<220> FEATURE:
<223> OTHER INFORMATION: R1GA/R2GC

<400> SEQUENCE: 21
aagcgcctca tcagcggtaa ccatcacggg ttcgggtgcg aaaaaccatg ccataacagg      60
aatgttcctt tcgaaaattg aggaagcctt atgcccttca accctactta gctgccaatt     120
attccgggct tgtgacccgc tacccgataa ataggtcggc tgaaaaattt cgttgcaata     180
tcaacaaaaa ggcctatcat tgggaggtgt cgcaccaagt acttttgcga agcgccatct     240
gacggatttt caaagatgt atatgctcgg tgcggaaacc tacgaaagga gattttaccc      300
atggctgtat acgaactccc agaactcgac tacgcatacg acgaaggag cacaaa         356

<210> SEQ ID NO 22
<211> LENGTH: 356
<212> TYPE: DNA
<213> ORGANISM: Artificial Sequence
<220> FEATURE:
<223> OTHER INFORMATION: R1GA/R2GG

<400> SEQUENCE: 22
aagcgcctca tcagcggtaa ccatcacggg ttcgggtgcg aaaaaccatg ccataacagg      60
aatgttcctt tcgaaaattg aggaagcctt atgcccttca accctactta gctgccaatt     120
attccgggct tgtgacccgc tacccgataa ataggtcggc tgaaaaattt cgttgcaata     180
tcaacaaaaa ggcctatcat tgggaggtgt cgcaccaagt acttttgcga agcgccatct     240
gacggatttt caaagatgt atatgctcgg tgcggaaacc tacgaaagga gattttaccc      300
atggctgtat acgaactccc agaactcgac tacgcatacg acgaaggag gacaaa         356

<210> SEQ ID NO 23
<211> LENGTH: 356
<212> TYPE: DNA
<213> ORGANISM: Artificial Sequence
<220> FEATURE:
<223> OTHER INFORMATION: R1GT/R2TT

<400> SEQUENCE: 23
aagcgcctca tcagcggtaa ccatcacggg ttcgggtgcg aaaaaccatg ccataacagg      60
aatgttcctt tcgaaaattg aggaagcctt atgcccttca accctactta gctgccaatt     120
attccgggct tgtgacccgc tacccgataa ataggtcggc tgaaaaattt cgttgcaata     180
tcaacaaaaa ggcctatcat tgggaggtgt cgcaccaagt acttttgcga agcgccatct     240
gacggatttt caaagatgt atatgctcgg tgcggaaacc tacgaaagga gtttttaccc      300
atggctgtat acgaactccc agaactcgac tacgcatacg acgaaggat tacaaa         356

<210> SEQ ID NO 24
<211> LENGTH: 356
<212> TYPE: DNA
<213> ORGANISM: Artificial Sequence
<220> FEATURE:
<223> OTHER INFORMATION: R1GT/R2GA

<400> SEQUENCE: 24
aagcgcctca tcagcggtaa ccatcacggg ttcgggtgcg aaaaaccatg ccataacagg      60
aatgttcctt tcgaaaattg aggaagcctt atgcccttca accctactta gctgccaatt     120
attccgggct tgtgacccgc tacccgataa ataggtcggc tgaaaaattt cgttgcaata     180
tcaacaaaaa ggcctatcat tgggaggtgt cgcaccaagt acttttgcga agcgccatct     240
```

```
gacggatttt caaaagatgt atatgctcgg tgcggaaacc tacgaaagga gttttacccc    300
atggctgtat acgaactccc agaactcgac tacgcatacg acgaaggag aacaaa         356
```

<210> SEQ ID NO 25
<211> LENGTH: 356
<212> TYPE: DNA
<213> ORGANISM: Artificial Sequence
<220> FEATURE:
<223> OTHER INFORMATION: R1GT/R2GT

<400> SEQUENCE: 25

```
aagcgcctca tcagcggtaa ccatcacggg ttcgggtgcg aaaaaccatg cctaacagg      60 aatgttcctt tcgaaaattg aggaagcctt atgcccttca accctactta gctgccaatt    120
attccgggct tgtgacccgc tacccgataa ataggtcggc tgaaaaattt cgttgcaata    180
tcaacaaaaa ggcctatcat tgggaggtgt cgcaccaagt acttttgcga agcgccatct    240
gacggatttt caaaagatgt atatgctcgg tgcggaaacc tacgaaagga gttttacccc    300
atggctgtat acgaactccc agaactcgac tacgcatacg acgaaggag tacaaa         356
```

<210> SEQ ID NO 26
<211> LENGTH: 356
<212> TYPE: DNA
<213> ORGANISM: Artificial Sequence
<220> FEATURE:
<223> OTHER INFORMATION: R1GT/R2GC

<400> SEQUENCE: 26

```
aagcgcctca tcagcggtaa ccatcacggg ttcgggtgcg aaaaaccatg cctaacagg      60 aatgttcctt tcgaaaattg aggaagcctt atgcccttca accctactta gctgccaatt    120
attccgggct tgtgacccgc tacccgataa ataggtcggc tgaaaaattt cgttgcaata    180
tcaacaaaaa ggcctatcat tgggaggtgt cgcaccaagt acttttgcga agcgccatct    240
gacggatttt caaaagatgt atatgctcgg tgcggaaacc tacgaaagga gttttacccc    300
atggctgtat acgaactccc agaactcgac tacgcatacg acgaaggag cacaaa         356
```

<210> SEQ ID NO 27
<211> LENGTH: 356
<212> TYPE: DNA
<213> ORGANISM: Artificial Sequence
<220> FEATURE:
<223> OTHER INFORMATION: R1GT/R2GG

<400> SEQUENCE: 27

```
aagcgcctca tcagcggtaa ccatcacggg ttcgggtgcg aaaaaccatg cctaacagg      60 aatgttcctt tcgaaaattg aggaagcctt atgcccttca accctactta gctgccaatt    120
attccgggct tgtgacccgc tacccgataa ataggtcggc tgaaaaattt cgttgcaata    180
tcaacaaaaa ggcctatcat tgggaggtgt cgcaccaagt acttttgcga agcgccatct    240
gacggatttt caaaagatgt atatgctcgg tgcggaaacc tacgaaagga gttttacccc    300
atggctgtat acgaactccc agaactcgac tacgcatacg acgaaggag gacaaa         356
```

<210> SEQ ID NO 28
<211> LENGTH: 356
<212> TYPE: DNA
<213> ORGANISM: Artificial Sequence
<220> FEATURE:
<223> OTHER INFORMATION: R1GC/R2TT

<400> SEQUENCE: 28

```
aagcgcctca tcagcggtaa ccatcacggg ttcgggtgcg aaaaaccatg ccataacagg    60
aatgttcctt tcgaaaattg aggaagcctt atgcccttca accctactta gctgccaatt   120
attccgggct tgtgacccgc tacccgataa ataggtcggc tgaaaatttt cgttgcaata   180
tcaacaaaaa ggcctatcat tgggaggtgt cgcaccaagt acttttgcga agcgccatct   240
gacggatttt caaagatgt atatgctcgg tgcggaaacc tacgaaagga gcttttaccc   300
atggctgtat acgaactccc agaactcgac tacgcatacg acgaaggat tacaaa        356
```

<210> SEQ ID NO 29
<211> LENGTH: 356
<212> TYPE: DNA
<213> ORGANISM: Artificial Sequence
<220> FEATURE:
<223> OTHER INFORMATION: R1GC/R2GA

<400> SEQUENCE: 29

```
aagcgcctca tcagcggtaa ccatcacggg ttcgggtgcg aaaaaccatg ccataacagg    60
aatgttcctt tcgaaaattg aggaagcctt atgcccttca accctactta gctgccaatt   120
attccgggct tgtgacccgc tacccgataa ataggtcggc tgaaaatttt cgttgcaata   180
tcaacaaaaa ggcctatcat tgggaggtgt cgcaccaagt acttttgcga agcgccatct   240
gacggatttt caaagatgt atatgctcgg tgcggaaacc tacgaaagga gcttttaccc   300
atggctgtat acgaactccc agaactcgac tacgcatacg acgaaggag aacaaa        356
```

<210> SEQ ID NO 30
<211> LENGTH: 356
<212> TYPE: DNA
<213> ORGANISM: Artificial Sequence
<220> FEATURE:
<223> OTHER INFORMATION: R1GC/R2GT

<400> SEQUENCE: 30

```
aagcgcctca tcagcggtaa ccatcacggg ttcgggtgcg aaaaaccatg ccataacagg    60
aatgttcctt tcgaaaattg aggaagcctt atgcccttca accctactta gctgccaatt   120
attccgggct tgtgacccgc tacccgataa ataggtcggc tgaaaatttt cgttgcaata   180
tcaacaaaaa ggcctatcat tgggaggtgt cgcaccaagt acttttgcga agcgccatct   240
gacggatttt caaagatgt atatgctcgg tgcggaaacc tacgaaagga gcttttaccc   300
atggctgtat acgaactccc agaactcgac tacgcatacg acgaaggag tacaaa        356
```

<210> SEQ ID NO 31
<211> LENGTH: 356
<212> TYPE: DNA
<213> ORGANISM: Artificial Sequence
<220> FEATURE:
<223> OTHER INFORMATION: R1GC/R2GC

<400> SEQUENCE: 31

```
aagcgcctca tcagcggtaa ccatcacggg ttcgggtgcg aaaaaccatg ccataacagg    60
aatgttcctt tcgaaaattg aggaagcctt atgcccttca accctactta gctgccaatt   120
attccgggct tgtgacccgc tacccgataa ataggtcggc tgaaaatttt cgttgcaata   180
tcaacaaaaa ggcctatcat tgggaggtgt cgcaccaagt acttttgcga agcgccatct   240
gacggatttt caaagatgt atatgctcgg tgcggaaacc tacgaaagga gcttttaccc   300
atggctgtat acgaactccc agaactcgac tacgcatacg acgaaggag cacaaa        356
```

<210> SEQ ID NO 32
<211> LENGTH: 356
<212> TYPE: DNA
<213> ORGANISM: Artificial Sequence
<220> FEATURE:
<223> OTHER INFORMATION: R1GC/R2GG

<400> SEQUENCE: 32

```
aagcgcctca tcagcggtaa ccatcacggg ttcgggtgcg aaaaaccatg ccataacagg    60
aatgttcctt tcgaaaattg aggaagcctt atgcccttca accctactta gctgccaatt   120
attccgggct tgtgacccgc tacccgataa ataggtcggc tgaaaaattt cgttgcaata   180
tcaacaaaaa ggcctatcat tgggaggtgt cgcaccaagt acttttgcga agcgccatct   240
gacggatttt caaagatgt atatgctcgg tgcggaaacc tacgaaagga gcttttaccc    300
atggctgtat acgaactccc agaactcgac tacgcatacg acgaaggag gacaaa        356
```

<210> SEQ ID NO 33
<211> LENGTH: 289
<212> TYPE: PRT
<213> ORGANISM: Artificial Sequence
<220> FEATURE:
<223> OTHER INFORMATION: amino acid sequence of an enzyme protein
      originated from Clostridium scindens

<400> SEQUENCE: 33

```
Met Lys His Gly Ile Tyr Tyr Ala Tyr Trp Glu Gln Glu Trp Ala Ala
1               5                   10                  15

Asp Tyr Lys Arg Tyr Val Glu Lys Ala Lys Leu Gly Phe Asp Ile
            20                  25                  30

Leu Glu Val Gly Ala Ala Pro Leu Pro Asp Tyr Ser Ala Gln Glu Val
        35                  40                  45

Lys Glu Leu Lys Lys Cys Ala Asp Asp Asn Gly Ile Gln Leu Thr Ala
    50                  55                  60

Gly Tyr Gly Pro Ala Phe Asn His Asn Met Gly Ser Ser Asp Pro Lys
65                  70                  75                  80

Ile Arg Glu Glu Ala Leu Gln Trp Tyr Lys Arg Leu Phe Glu Val Met
                85                  90                  95

Ala Gly Leu Asp Ile His Leu Ile Gly Gly Ala Leu Tyr Ser Tyr Trp
            100                 105                 110

Pro Val Asp Phe Ala Thr Ala Asn Lys Glu Glu Asp Trp Lys His Ser
        115                 120                 125

Val Glu Gly Met Gln Ile Leu Ala Pro Ile Ala Ser Gln Tyr Gly Ile
    130                 135                 140

Asn Leu Gly Met Glu Val Leu Asn Arg Phe Glu Ser His Ile Leu Asn
145                 150                 155                 160

Thr Ser Glu Glu Gly Val Lys Phe Val Thr Glu Val Gly Met Asp Asn
                165                 170                 175

Val Lys Val Met Leu Asp Thr Phe His Met Asn Ile Glu Glu Ser Ser
            180                 185                 190

Ile Gly Asp Ala Ile Arg His Ala Gly Lys Leu Leu Gly His Phe His
        195                 200                 205

Thr Gly Glu Cys Asn Arg Met Val Pro Gly Lys Gly Arg Thr Pro Trp
    210                 215                 220

Arg Glu Ile Gly Asp Ala Leu Arg Glu Ile Glu Tyr Asp Gly Thr Val
225                 230                 235                 240
```

```
Val Met Glu Pro Phe Val Arg Met Gly Gly Gln Val Gly Ser Asp Ile
            245                 250                 255

Lys Val Trp Arg Asp Ile Ser Lys Gly Ala Gly Glu Asp Arg Leu Asp
        260                 265                 270

Glu Asp Ala Arg Arg Ala Val Glu Phe Gln Arg Tyr Met Leu Glu Trp
        275                 280                 285

Lys

<210> SEQ ID NO 34
<211> LENGTH: 295
<212> TYPE: PRT
<213> ORGANISM: Artificial Sequence
<220> FEATURE:
<223> OTHER INFORMATION: amino acid sequence of psicose 3-epimerase from
      Treponema primitia

<400> SEQUENCE: 34

Met Gln Tyr Gly Ile Tyr Phe Ala Tyr Trp Thr Lys Glu Trp Gln Ala
1               5                   10                  15

Asp Tyr Lys Lys Tyr Ile Asp Lys Val Ser Lys Leu Gly Phe Asp Ile
            20                  25                  30

Leu Glu Ile Ser Cys Ala Ala Leu Lys Asp Gln Tyr Val Ser Asp Ser
        35                  40                  45

Gln Leu Phe Asp Leu Arg Asp Tyr Ala Lys Glu Lys Gly Val Thr Leu
50                  55                  60

Thr Ala Gly Tyr Gly Pro Ala Lys Gly Glu Asn Leu Ser Ser Ser Asp
65                  70                  75                  80

Asn Arg Val Val Lys Asn Ala Lys Ala Phe Tyr Lys Asp Val Leu Gly
                85                  90                  95

Lys Leu Asn Lys Leu Asp Ile Arg Leu Leu Gly Gly Gly Leu Tyr Ser
            100                 105                 110

Tyr Trp Pro Val Asp Tyr Ser Leu Pro Ile Asp Lys Ala Gly Asp Trp
        115                 120                 125

Lys Arg Ser Val Glu Asn Ile Arg Glu Ile Ala Ala Ile Ala Ala Asp
130                 135                 140

Arg Asn Val Val Leu Gly Met Glu Val Leu Asn Arg Phe Glu Gly Tyr
145                 150                 155                 160

Leu Leu Asn Thr Cys Glu Glu Gly Ile Lys Phe Val Asp Glu Val Asn
                165                 170                 175

His Pro Asn Val Lys Val Met Leu Asp Thr Phe His Met Asn Ile Glu
            180                 185                 190

Glu Asp Asn Met Ala Glu Ala Ile Arg Met Ala Gly Asp Lys Leu Gly
        195                 200                 205

His Phe His Ile Gly Glu Gln Asn Arg Lys Val Pro Gly Lys Gly Cys
210                 215                 220

Ile Pro Trp Asn Ala Ile Gly His Ala Leu Arg Asp Ile Arg Tyr Asn
225                 230                 235                 240

Gly Thr Val Val Met Glu Pro Phe Val Met Pro Gly Gly Thr Ile Gly
                245                 250                 255

Gln Asp Ile Lys Val Trp Arg Asn Leu Leu Pro Glu Thr Ser Glu Thr
            260                 265                 270

Ile Leu Asp Arg Asp Ala Lys Gly Ala Leu Glu Phe Val Lys His Val
        275                 280                 285

Phe Gly Ser Thr Ser Val Leu
290                 295
```

<210> SEQ ID NO 35
<211> LENGTH: 282
<212> TYPE: PRT
<213> ORGANISM: Artificial Sequence
<220> FEATURE:
<223> OTHER INFORMATION: amino acid sequence of D-psicose 3-epimerase originated from Ensifer adhaerens

<400> SEQUENCE: 35

```
Met Gln Gly Phe Gly Val His Thr Ser Met Trp Thr Met Asn Trp Asp
1               5                   10                  15

Arg Pro Gly Ala Glu Arg Ala Val Ala Ala Val Lys Tyr Ala Val
            20                  25                  30

Asp Phe Ile Glu Ile Pro Met Leu Asn Pro Ala Val Asp Thr Ala
        35                  40                  45

His Thr Arg Ala Leu Leu Glu Lys Asn Lys Leu Arg Ala Val Cys Ser
    50                  55                  60

Leu Gly Leu Pro Glu Arg Ala Trp Ala Ser Val Arg Pro Asp Ala Ala
65                  70                  75                  80

Ile Glu His Leu Lys Val Ala Ile Asp Lys Thr Ala Asp Leu Gly Gly
                85                  90                  95

Glu Ala Leu Ser Gly Val Ile Tyr Gly Gly Ile Gly Glu Arg Thr Gly
            100                 105                 110

Val Pro Pro Thr Glu Ala Glu Tyr Asp Asn Ile Ala Arg Val Leu Gln
        115                 120                 125

Ala Ala Ala Lys His Ala Lys Thr Arg Gly Ile Glu Leu Gly Val Glu
    130                 135                 140

Ala Val Asn Arg Tyr Glu Asn His Leu Ile Asn Thr Gly Trp Gln Ala
145                 150                 155                 160

Val Asp Met Ile Lys Arg Val Gly Ala Asp Asn Val Phe Val His Leu
                165                 170                 175

Asp Thr Tyr His Met Asn Ile Glu Glu Lys Gly Ile Gly Thr Gly Ile
            180                 185                 190

Leu Asp Ala Arg Asp Phe Ile Lys Tyr Ile His Leu Ser Glu Ser Asp
        195                 200                 205

Arg Gly Thr Pro Gly Tyr Gly Asn Cys Ala Trp Asp Glu Ile Phe Ala
    210                 215                 220

Thr Leu Ala Ala Ile Gly Phe Lys Gly Gly Leu Ala Met Glu Ser Phe
225                 230                 235                 240

Ile Asn Met Pro Pro Glu Val Ala Tyr Gly Leu Ala Val Trp Arg Pro
                245                 250                 255

Val Ala Arg Asp Glu Glu Glu Val Met Gly Asn Gly Leu Pro Phe Leu
            260                 265                 270

Arg Asn Lys Ala Arg Gln Tyr Gly Leu Ile
        275                 280
```

<210> SEQ ID NO 36
<211> LENGTH: 290
<212> TYPE: PRT
<213> ORGANISM: Artificial Sequence
<220> FEATURE:
<223> OTHER INFORMATION: amino acid sequence of D-psicose 3-epimerase originated from Ruminococcus torques

<400> SEQUENCE: 36

```
Met Lys Met Lys Phe Gly Thr Leu Tyr Ser Tyr Trp Gly Thr Lys Trp
1               5                   10                  15
```

Gln Cys Asp Tyr Leu Lys Thr Leu Lys Arg Val Ser Asp Ile Gly Phe
            20                  25                  30

Asp Ile Leu Glu Met Gly Ala Pro His Leu Leu Glu Met Ser Asp Tyr
        35                  40                  45

Glu Leu Ser Glu Leu Arg Arg Ala Ala Lys Asp Met Asp Met Val Leu
    50                  55                  60

Thr Ala Asn Ile Gly Pro Ala Lys Asp Lys Asp Leu Ala Ser Pro Asp
65                  70                  75                  80

Pro Asp Ile Arg Lys Ala Gly Val Asn Tyr Leu Ile Asp Ile Leu Lys
                85                  90                  95

Ala Met Glu Lys Val Gly Ser Lys Ser Leu Val Gly Ala Met Tyr Ser
            100                 105                 110

Tyr Trp Pro Cys Gln Phe Glu Ile Thr Asp Lys Glu Ala Ala Trp Glu
        115                 120                 125

Arg Ser Ile Glu Gly Met Lys Glu Val Ala Glu Ala Ala Glu Ser Leu
    130                 135                 140

Gly Ile Glu Cys Cys Gln Glu Val Leu Asn Arg Tyr Glu Thr Tyr Ile
145                 150                 155                 160

Ile Thr Asp Cys Arg Glu Gly Leu Glu Tyr Cys Arg Arg Val Gly Ser
                165                 170                 175

Glu Asn Val Asn Leu Leu Leu Asp Thr Phe His Met Asn Ile Glu Glu
            180                 185                 190

Asp Asn Ile Pro Glu Ala Ile Arg Leu Ala Gly Arg Lys Leu Gly His
        195                 200                 205

Leu His Val Gly Glu Ser Asn Arg Lys Leu Pro Gly Met Gly Ser Leu
    210                 215                 220

Pro Trp Arg Asp Ile Gly Arg Ala Leu Arg Asp Ile Gly Tyr Glu Lys
225                 230                 235                 240

Gly Val Val Met Glu Pro Phe Leu Leu Gln Gly Gly Glu Val Ala Arg
                245                 250                 255

Asp Cys Lys Val Trp Arg Asp Leu Ser Gly Asn Ala Asp Glu Lys Met
            260                 265                 270

Leu Asp Arg Tyr Ile Lys Glu Ser Leu Thr Phe Leu Lys His Glu Phe
        275                 280                 285

Thr Phe
    290

<210> SEQ ID NO 37
<211> LENGTH: 870
<212> TYPE: DNA
<213> ORGANISM: Artificial Sequence
<220> FEATURE:
<223> OTHER INFORMATION: modified nucleic acid sequence (1) of the
      enzyme protein of SEQ ID NO: 33

<400> SEQUENCE: 37
atgaaacacg gtatctacta cgcgtactgg gaacaggaat gggcggcgga ctacaaacgt      60
tacgttgaaa aagcggcgaa actgggtttc gacatcctgg aagttggtgc ggcgccgctg     120
ccggactact ctgcgcagga agttaaagaa ctgaaaaaat gcgcggacga caacggtatc     180
cagctgaccg cgggttacgg tccggcgttc aaccacaaca tgggttcttc tgaccccgaaa    240 atccgtgaag aagcgctgca gtggtacaaa cgtctgttcg aagttatggc gggtctggac    300
atccacctga cggtggtgc gctgtactct tactggccgg ttgacttcgc gaccgcgaac     360
aaagaagaag actggaaaca ctctgttgaa ggtatgcaga tcctggcgcc gatcgcgtct    420

| | |
|---|---|
| cagtacggta tcaacctggg tatggaagtt ctgaaccgtt tcgaatctca catcctgaac | 480 |
| acctctgaag aaggtgttaa attcgttacc gaagttggta tggacaacgt taaagttatg | 540 |
| ctggacacct tccacatgaa catcgaagaa tcttctatcg gtgacgcgat ccgtcacgcg | 600 |
| ggtaaactgc tgggtcactt ccacaccggt gaatgcaacc gtatggttcc gggtaaaggt | 660 |
| cgtaccccgt ggcgtgaaat cggtgacgcg ctgcgtgaaa tcgaatacga cggtaccgtt | 720 |
| gttatggaac cgttcgttcg tatgggtggt caggttggtt ctgacatcaa agtttggcgt | 780 |
| gacatctcta aaggtgcggg tgaagaccgt ctggacgaag acgcgcgtcg tgcggttgaa | 840 |
| ttccagcgtt acatgctgga atggaaataa | 870 |

<210> SEQ ID NO 38
<211> LENGTH: 870
<212> TYPE: DNA
<213> ORGANISM: Artificial Sequence
<220> FEATURE:
<223> OTHER INFORMATION: modified nucleic acid sequence (2) of the
      enzyme protein of SEQ ID NO: 33

<400> SEQUENCE: 38

| | |
|---|---|
| atgaagcacg gcatctacta cgcatactgg gagcaggagt gggcagcaga ctacaagcgc | 60 |
| tacgttgaga aggcagcaaa gctgggcttc gacatcctgg aggttggcgc agcaccactg | 120 |
| ccagactact ccgcacagga ggttaaggag ctgaagaagt gcgcagacga caacggcatc | 180 |
| cagctgaccg caggctacgg cccagcattc aaccacaaca tgggctcctc cgacccaaag | 240 |
| atccgcgagg aggcactgca gtggtacaag cgcctgttcg aggttatggc aggcctggac | 300 |
| atccacctga tcggcggcgc actgtactcc tactggccag ttgacttcgc aaccgcaaac | 360 |
| aaggaggagg actggaagca ctccgttgag ggcatgcaga tcctggcacc aatcgcatcc | 420 |
| cagtacggca tcaacctggg catggaggtt ctgaaccgct tcgagtccca catcctgaac | 480 |
| acctccgagg agggcgttaa gttcgttacc gaggttggca tggacaacgt taaggttatg | 540 |
| ctggacacct tccacatgaa catcgaggag tcctccatcg gcgacgcaat ccgccacgca | 600 |
| ggcaagctgc tgggccactt ccacaccggc gagtgcaacc gcatggttcc aggcaagggc | 660 |
| cgcacccgat ggcgcgagat cggcgacgca ctgcgcgaga tcgagtacga cggcaccgtt | 720 |
| gttatggagc cattcgttcg catgggcggc caggttggct ccgacatcaa ggtttggcgc | 780 |
| gacatctcca agggcgcagg cgaggaccgc ctggacgagg acgcacgccg cgcagttgag | 840 |
| ttccagcgct acatgctgga gtggaagtaa | 870 |

<210> SEQ ID NO 39
<211> LENGTH: 888
<212> TYPE: DNA
<213> ORGANISM: Artificial Sequence
<220> FEATURE:
<223> OTHER INFORMATION: modified nucleic acid sequence (1) of the
      enzyme protein of SEQ ID NO: 34

<400> SEQUENCE: 39

| | |
|---|---|
| atgcagtacg gtatctactt cgcgtactgg accaaagaat ggcaggcgga ctacaaaaaa | 60 |
| tacatcgaca agtttctaa actgggtttc gacatcctgg aaatctcttg cgcggcgctg | 120 |
| aaagaccagt acgtttctga ctctcagctg ttcgacctgc gtgactacgc gaaagaaaaa | 180 |
| ggtgttaccc tgaccgcggg ttacggtccg gcgaaaggtg aaaacctgtc ttcttctgac | 240 |
| aaccgtgttg ttaaaaacgc gaaagcgttc tacaaagact tctgggtaa actgaacaaa | 300 |
| ctggacatcc gtctgctggg tggtggtctg tactcttact ggccggttga ctactctctg | 360 |

```
ccgatcgaca aagcgggtga ctggaaacgt tctgttgaaa acatccgtga atcgcggcg     420 atcgcggcgg accgtaacgt tgttctgggt atggaagttc tgaaccgttt cgaaggttac    480
ctgctgaaca cctgcgaaga aggtatcaaa ttcgttgacg aagttaacca cccgaacgtt    540
aaagttatgc tggacacctt ccacatgaac atcgaagaag acaacatggc ggaagcgatc    600
cgtatggcgg gtgacaaact gggtcacttc cacatcggtg aacagaaccg taaagttccg    660
ggtaaaggtt gcatcccgtg aacgaaatc ggtcacgcgc tgcgtgacat ccgttacaac    720
ggtaccgttg ttatggaacc gttcgttatg ccgggtggta ccatcggtca ggacatcaaa    780
gtttggcgtg acctgctgcc ggaaacctct gaaaccatcc tggaccgtga cgcgaaaggt    840
gcgctggaat tcgttaaaca cgttttcggt tctacctctg ttctgtaa                 888
```

<210> SEQ ID NO 40
<211> LENGTH: 888
<212> TYPE: DNA
<213> ORGANISM: Artificial Sequence
<220> FEATURE:
<223> OTHER INFORMATION: modified nucleic acid sequence (2) of the
      enzyme protein of SEQ ID NO: 34

<400> SEQUENCE: 40

```
atgcagtacg gcatctactt cgcatactgg accaaggagt ggcaggcaga ctacaagaag    60
tacatcgaca aggtttccaa gctgggcttc gacatcctgg agatctcctg cgcagcactg    120
aaggaccagt acgttccga ctcccagctg ttcgacctgc gcgactacgc aaaggagaag    180
ggcgttaccc tgaccgcagg ctacggccca gcaaagggcg agaacctgtc ctcctccgac    240
aaccgcgttg ttaagaacgc aaaggcattc tacaaggacg ttctgggcaa gctgaacaag    300
ctggacatcc gcctgctggg cggcggcctg tactcctact ggccagttga ctactccctg    360
ccaatcgaca aggcaggcga ctggaagcgc tccgttgaga acatccgcga gatcgcagca    420
atcgcagcag accgcaacgt tgttctgggc atggaggttc tgaaccgctt cgagggctac    480
ctgctgaaca cctgcgagga gggcatcaag ttcgttgacg aggttaacca cccaaacgtt    540
aaggttatgc tggacacctt ccacatgaac atcgaggagg acaacatggc agaggcaatc    600
cgcatggcag gcgacaagct gggccacttc cacatcggcg agcagaaccg caaggttcca    660
ggcaagggct gcatcccatg aacgagatc ggccacgcac tgcgcgacat ccgctacaac    720
ggcaccgttg ttatggagcc attcgttatg ccaggcggca ccatcggcca ggacatcaag    780
gtttggcgcg acctgctgcc agagacctcc gagaccatcc tggaccgcga cgcaaagggc    840
gcactggagt tcgttaagca cgttttcggc tccacctccg ttctgtaa                 888
```

<210> SEQ ID NO 41
<211> LENGTH: 855
<212> TYPE: DNA
<213> ORGANISM: Artificial Sequence
<220> FEATURE:
<223> OTHER INFORMATION: modified nucleic acid sequence (1) of the
      enzyme protein of SEQ ID NO: 35

<400> SEQUENCE: 41

```
atgcagggtt tcggtgttca cacctctatg tggaccatga actgggaccg tccgggtgcg    60
gaacgtgcgg ttgcggcggc ggttaaatac gcggttgact tcatcgaaat cccgatgctg    120
aacccgccgg cggttgacac cgcgcacacc cgtgcgctgc tggaaaaaaa caaactgcgt    180
gcggtttgct ctctgggtct gccggaacgt gcgtgggcgt ctgttcgtcc ggacgcggcg    240
```

```
atcgaacacc tgaaagttgc gatcgacaaa accgcggacc tgggtggtga agcgctgtct    300
ggtgttatct acggtggtat cggtgaacgt accggtgttc cgccgaccga agcggaatac    360
gacaacatcg cgcgtgttct gcaggcggcg gcgaaacacg cgaaacccg tggtatcgaa     420 ctgggtgttg aagcggttaa ccgttacgaa aaccacctga tcaacaccgg ttggcaggcg    480
gttgacatga tcaaacgtgt tggtgcggac aacgttttcg ttcacctgga cacctaccac    540
atgaacatcg aagaaaaagg tatcggtacc ggtatcctgg acgcgcgtga cttcatcaaa    600
tacatccacc tgtctgaatc tgaccgtggt accccgggtt acggtaactg cgcgtgggac    660
gaaatcttcg cgaccctggc ggcgatcggt ttcaaaggtg gtctggcgat ggaatctttc    720
atcaacatgc cgccggaagt tgcgtacggt ctggcggttt ggcgtccggt tgcgcgtgac    780
gaagaagaag ttatgggtaa ctctctgccg ttcctgcgta caaagcgcg tcagtacggt     840 ctgatcctgg aataa                                                     855

<210> SEQ ID NO 42
<211> LENGTH: 855
<212> TYPE: DNA
<213> ORGANISM: Artificial Sequence
<220> FEATURE:
<223> OTHER INFORMATION: modified nucleic acid sequence (2) of the
      enzyme protein of SEQ ID NO: 35

<400> SEQUENCE: 42
atgcagggct tcggcgttca cacctccatg tggaccatga actgggaccg cccaggcgca     60
gagcgcgcag ttgcagcagc agttaagtac gcagttgact tcatcgagat cccaatgctg    120
aacccaccag cagttgacac cgcacacacc cgcgcactgc tggagaagaa caagctgcgc    180
gcagtttgct ccctgggcct gccagagcgc gcatgggcat ccgttcgccc agacgcagca    240
atcgagcacc tgaaggttgc aatcgacaag accgcagacc tgggcggcga ggcactgtcc    300
ggcgttatct acggcggcat cggcgagcgc accggcgttc caccaaccga ggcagagtac    360
gacaacatcg cacgcgttct gcaggcagca gcaaagcacg caaagacccg cggcatcgag    420
ctgggcgttg aggcagttaa ccgctacgag aaccacctga tcaacaccgg ctggcaggca    480
gttgacatga tcaagcgcgt tggcgcagac aacgttttcg ttcacctgga cacctaccac    540
atgaacatcg aggagaaggg catcggcacc ggcatcctgg acgcacgcga cttcatcaag    600
tacatccacc tgtccgagtc cgaccgcggc accccaggct acggcaactg cgcatgggac    660
gagatcttcg caaccctggc agcaatcggc ttcaagggcg gcctggcaat ggagtccttc    720
atcaacatgc caccagaggt tgcatacggc ctggcagttt ggcgcccagt tgcacgcgac    780
gaggaggagg ttatgggcaa ctccctgcca ttcctgcgca caaggcacg ccagtacggc     840 ctgatcctgg agtaa                                                     855

<210> SEQ ID NO 43
<211> LENGTH: 873
<212> TYPE: DNA
<213> ORGANISM: Artificial Sequence
<220> FEATURE:
<223> OTHER INFORMATION: modified nucleic acid sequence (1) of the
      enzyme protein of SEQ ID NO: 36

<400> SEQUENCE: 43
atgaaaatga aattcggtac cctgtactct tactggggta ccaaatggca gtgcgactac     60
ctgaaaaccc tgaacgtgt ttctgacatc ggtttcgaca tcctggaaat gggtgcgccg    120
cacctgctgg aaatgtctga ctacgaactg tctgaactgc gtcgtgcggc gaaagacatg    180
```

```
gacatggttc tgaccgcgaa catcggtccg gcgaaagaca aagacctggc gtctccggac    240
ccggacatcc gtaaagcggg tgttaactac ctgatcgaca tcctgaaagc gatggaaaaa    300
gttggttcta aatctctggt tggtgcgatg tactcttact ggccgtgcca gttcgaaatc    360
accgacaaag aagcggcgtg ggaacgttct atcgaaggta tgaaagaagt tgcggaagcg    420
gcggaatctc tgggtatcga atgctgccag gaagttctga accgttacga aacctacatc    480
atcaccgact gccgtgaagg tctggaatac tgccgtcgtg ttggttctga aaacgttaac    540
ctgctgctgg acaccttcca catgaacatc gaagaagaca catcccggaa gcgatccgt     600 ctggcgggtc gtaaactggg tcacctgcac gttggtgaat ctaaccgtaa actgccgggt    660
atgggttctc tgccgtggcg tgacatcggt cgtgcgctgc gtgacatcgg ttacgaaaaa    720
ggtgttgtta tggaaccgtt cctgctgcag ggtggtgaag ttgcgcgtga ctgcaaagtt    780
tggcgtgacc tgtctggtaa cgcggacgaa aaaatgctgg accgttacat caaagaatct    840
ctgaccttcc tgaaacacga attcaccttc tga                                 873

<210> SEQ ID NO 44
<211> LENGTH: 873
<212> TYPE: DNA
<213> ORGANISM: Artificial Sequence
<220> FEATURE:
<223> OTHER INFORMATION: modified nucleic acid sequence (2) of the
      enzyme protein of SEQ ID NO: 36

<400> SEQUENCE: 44
atgaagatga aatttggaac attatattct tattggggaa caaaatggca atgtgattat     60
ttgaaaacat taaaacgagt ttcagacatc ggatttgaca ttttggaaat gggtgctcct    120
cacttgttgg aaatgtcaga ttatgaactt tcagaattga ggcgcgcggc gaaagatatg    180
gatatggtat tgacggcaaa tatcggaccg gcaaagata aagatcttgc ttctcctgat    240
ccggatatac gaaaagcggg agtaaactat ttgatcgata tattaaaagc aatggaaaaa    300
gtaggatcta aatcacttgt tggagcaatg tattcttatt ggccgtgtca atttgaaata    360
acggataagg aagctgcctg ggagagaagc atcgagggga tgaaagaggt tgcagaagct    420
gcggaatcat tgggaatcga atgctgtcag gaagttttga atcgatatga aacttatatt    480
atcacagatt gcagggaagg attggaatac tgcaggagag tcggaagtga aaacgttaat    540
ctccttcttg atacatttca tatgaatatc gaagaagata atattccgga ggctatccgg    600
cttgcaggaa gaaaattggg ccatctgcat gtgggagaat caaacagaaa gcttccggga    660
atgggatccc ttccttggag agatatcgga cgggcgctaa gagatatcgg atatgagaaa    720
ggcgtcgtta tggaaccgtt tcttcttcaa ggaggagagg tcgctcggga ctgtaaagtg    780
tggagagatt taagtgggaa tgcagatgag aaaatgctgg atcgctatat aaaagaatct    840
ttaacatttt tgaaacatga atttacgttt tga                                 873

<210> SEQ ID NO 45
<211> LENGTH: 48
<212> TYPE: DNA
<213> ORGANISM: Artificial Sequence
<220> FEATURE:
<223> OTHER INFORMATION: RBS1_F
<220> FEATURE:
<221> NAME/KEY: misc_feature
<222> LOCATION: (23)..(24)
<223> OTHER INFORMATION: n is independently selected from the group of
      A, T, G and C
```

<400> SEQUENCE: 45
ggtgcggaaa cctacgaaag ganntttac ccatggctgt atacgaac    48

<210> SEQ ID NO 46
<211> LENGTH: 48
<212> TYPE: DNA
<213> ORGANISM: Artificial Sequence
<220> FEATURE:
<223> OTHER INFORMATION: RBS1_R
<220> FEATURE:
<221> NAME/KEY: misc_feature
<222> LOCATION: (25)..(26)
<223> OTHER INFORMATION: n is independently selected from the group of
      A, T, G and C

<400> SEQUENCE: 46
gttcgtatac agccatgggt aaaanntcct ttcgtaggtt tccgcacc    48

<210> SEQ ID NO 47
<211> LENGTH: 50
<212> TYPE: DNA
<213> ORGANISM: Artificial Sequence
<220> FEATURE:
<223> OTHER INFORMATION: RBS2_F
<220> FEATURE:
<221> NAME/KEY: misc_feature
<222> LOCATION: (23)..(24)
<223> OTHER INFORMATION: n is independently selected from the group of
      A, T, G and C

<400> SEQUENCE: 47
gactacgcat acgacgaaag gannacaaaa tgaaacacgg tatctactac    50

<210> SEQ ID NO 48
<211> LENGTH: 50
<212> TYPE: DNA
<213> ORGANISM: Artificial Sequence
<220> FEATURE:
<223> OTHER INFORMATION: RBS2_R
<220> FEATURE:
<221> NAME/KEY: misc_feature
<222> LOCATION: (27)..(28)
<223> OTHER INFORMATION: n is independently selected from the group of
      A, T, G and C

<400> SEQUENCE: 48
gtagtagata ccgtgtttca ttttgtnntc ctttcgtcgt atgcgtagtc    50

<210> SEQ ID NO 49
<211> LENGTH: 48
<212> TYPE: DNA
<213> ORGANISM: Artificial Sequence
<220> FEATURE:
<223> OTHER INFORMATION: RBS1GT_F

<400> SEQUENCE: 49
ggtgcggaaa cctacgaaag gagttttac ccatggctgt atacgaac    48

<210> SEQ ID NO 50
<211> LENGTH: 48
<212> TYPE: DNA
<213> ORGANISM: Artificial Sequence
<220> FEATURE:
<223> OTHER INFORMATION: RBS1GT_R

<400> SEQUENCE: 50
gttcgtatac agccatgggt aaaaactcct ttcgtaggtt tccgcacc    48

<210> SEQ ID NO 51
<211> LENGTH: 48
<212> TYPE: DNA
<213> ORGANISM: Artificial Sequence
<220> FEATURE:
<223> OTHER INFORMATION: RBS1GC_F

<400> SEQUENCE: 51
ggtgcggaaa cctacgaaag gagcttttac ccatggctgt atacgaac                48

<210> SEQ ID NO 52
<211> LENGTH: 48
<212> TYPE: DNA
<213> ORGANISM: Artificial Sequence
<220> FEATURE:
<223> OTHER INFORMATION: RBS1GC_R

<400> SEQUENCE: 52
gttcgtatac agccatgggt aaaagctcct ttcgtaggtt tccgcacc                48

<210> SEQ ID NO 53
<211> LENGTH: 48
<212> TYPE: DNA
<213> ORGANISM: Artificial Sequence
<220> FEATURE:
<223> OTHER INFORMATION: RBS1GG_F

<400> SEQUENCE: 53
ggtgcggaaa cctacgaaag gaggttttac ccatggctgt atacgaac                48

<210> SEQ ID NO 54
<211> LENGTH: 48
<212> TYPE: DNA
<213> ORGANISM: Artificial Sequence
<220> FEATURE:
<223> OTHER INFORMATION: RBS1GG_R

<400> SEQUENCE: 54
gttcgtatac agccatgggt aaaacctcct ttcgtaggtt tccgcacc                48

<210> SEQ ID NO 55
<211> LENGTH: 50
<212> TYPE: DNA
<213> ORGANISM: Artificial Sequence
<220> FEATURE:
<223> OTHER INFORMATION: RBS1GA/RBS2GA_F

<400> SEQUENCE: 55
gactacgcat acgacgaaag gagaacaaaa tgaaacacgg tatctactac              50

<210> SEQ ID NO 56
<211> LENGTH: 50
<212> TYPE: DNA
<213> ORGANISM: Artificial Sequence
<220> FEATURE:
<223> OTHER INFORMATION: RBS1GA/RBS2GA_R

<400> SEQUENCE: 56
gtagtagata ccgtgtttca ttttgttctc ctttcgtcgt atgcgtagtc              50

<210> SEQ ID NO 57
<211> LENGTH: 50
<212> TYPE: DNA
<213> ORGANISM: Artificial Sequence
<220> FEATURE:
<223> OTHER INFORMATION: RBS1GA/RBS2GT_F

```
<400> SEQUENCE: 57
gactacgcat acgacgaaag gagtacaaaa tgaaacacgg tatctactac            50

<210> SEQ ID NO 58
<211> LENGTH: 50
<212> TYPE: DNA
<213> ORGANISM: Artificial Sequence
<220> FEATURE:
<223> OTHER INFORMATION: RBS1GA/RBS2GT_R

<400> SEQUENCE: 58
gtagtagata ccgtgtttca ttttgtactc ctttcgtcgt atgcgtagtc            50

<210> SEQ ID NO 59
<211> LENGTH: 50
<212> TYPE: DNA
<213> ORGANISM: Artificial Sequence
<220> FEATURE:
<223> OTHER INFORMATION: RBS1GA/RBS2GC_F

<400> SEQUENCE: 59
gactacgcat acgacgaaag gagcacaaaa tgaaacacgg tatctactac            50

<210> SEQ ID NO 60
<211> LENGTH: 50
<212> TYPE: DNA
<213> ORGANISM: Artificial Sequence
<220> FEATURE:
<223> OTHER INFORMATION: RBS1GA/RBS2GC_R

<400> SEQUENCE: 60
gtagtagata ccgtgtttca ttttgtgctc ctttcgtcgt atgcgtagtc            50

<210> SEQ ID NO 61
<211> LENGTH: 50
<212> TYPE: DNA
<213> ORGANISM: Artificial Sequence
<220> FEATURE:
<223> OTHER INFORMATION: RBS1GA/RBS2GG_F

<400> SEQUENCE: 61
gactacgcat acgacgaaag gaggacaaaa tgaaacacgg tatctactac            50

<210> SEQ ID NO 62
<211> LENGTH: 50
<212> TYPE: DNA
<213> ORGANISM: Artificial Sequence
<220> FEATURE:
<223> OTHER INFORMATION: RBS1GA/RBS2GG_R

<400> SEQUENCE: 62
gtagtagata ccgtgtttca ttttgtcctc ctttcgtcgt atgcgtagtc            50
```

EXPRESSION SYSTEM FOR PSICOSE EPIMERASE AND PRODUCTION FOR PSICOSE USING THE SAME

CROSS-REFERENCE TO RELATED APPLICATION

This application is a Divisional Application of U.S. patent application Ser. No. 14/927,731, which was filed on Oct. 30, 2015, which claims priority to and the benefit of Korean Patent Application No. 10-2014-0149019 filed Oct. 30, 2014, on and Korean Patent Application No. 10-2015-0072090 filed in the Korea Intellectual Property Office on May 22, 2015, the entire contents of which are incorporated herein by reference.

SEQUENCE LISTING

The contents of the of the electronic sequence listing created on Oct. 30, 2015, named PPP20190441US Sequence Listing.txt and 37,000 bytes in size, is hereby incorporated by reference in its entirety.

TECHNICAL FIELD

The present invention an expression system being capable of producing Psicose epimerase having a high conversion rate and stability, generally recognized as safe (GRAS) microorganism including the expression system, and a method of producing psicose by using the microorganism and the enzyme.

BACKGROUND ART

Various biosynthetic compounds are produced in the natural metabolic process and used in different industrial fields such as food, feedstuff, cosmetic, and pharmaceuticals. The compounds have been produced by using bacterium or other microorganism developed for producing and secreting them in a large scale. For examples, *Corynebacterium* species has been used in the industry of amino acid production. In middle of 1950, *Corynebacterium glutamicum* producing glutamic acid efficiently and, auxotrophic mutant of *Corynebacterium glutamicum* has produced various amino acids by using fermentation.

The expression of various related genes can be regulated accurately for cell engineering therefore requiring the efficient expression system. Different components of cell regulating sequence have been known in the art. The examples of the components are a binding region to the operator, a RNA polymerase binding region of −35 and −10 regions, and a ribosome binding site or Shine-Dalgarno sequence in ribosomal 16S RNA.

It is important to select a promoter to develop the expression system, because the promoter is largely involved in the gene expression level and expression regulation. Several promoters being applicable to *Corynebacterium glutamicum* have been reported and are derived from *Corynebacterium* sp. or *E. coli* (J. Biotechnol., 104:311-323, 2003).

However, the promoter derived from *E. coli* a low permeability of an expression inducer and absence of gene expression inhibitor and thus shows low activity relative to that of *Corynebacterium*. Even if the same promoters are used, their activities are different depending on the coating sequence of target gene. The promoters used in *Corynebacterium* have a difficulty in being prepared for the desired object, because it is a narrow of choice in the expression level of promoters. Especially, when the expressions of various genes are regulated together such as the establishment of metabolic pathway, *Corynebacterium*, various promoters cannot be selected, unlike *E. coli*.

Psicose is getting a spotlight in a diet sweetener, but is required to be produced in a large scale for applying to the food due to rare sugar in nature. In the prior art, Psicose has been largely produced by synthetic chemical method. As the enzymatic method, KR10-0744479 discloses the mass production of psicose using the psicose epimerase produced by *E. coli* transformed with the coding gene of psicose epimerase derived from *Agrobacterium tumefaciens*. There is a method of producing psicose by using a microorganism producing enzyme without purification in a low production cost. In the disclosure of KR10-1106253, the recombinant *E. coli* which is transformed with the coding gene of psicose-3-epimerase derived from *Agrobacterium tumefaciens* and includes an inactivated specific gene, is inoculated on the culture medium including fructose to convert the fructose to psicose.

The recombinant *E. coli* used in KR10-1106253 is not GRAS (Generally Recognized As Safe) microorganism, and thus cannot be suitable in food industry. In addition, the Psicose epimerase derived from *Agrobacterium tumefaciens* has a low enzyme activity and heat stability.

Therefore, there is a need to develop an expressing being capable of producing the Psicose epimerase having a high enzyme activity in GRAS microorganism at a high yield and stably expression system, a method of psicose epimerase using the expression system, and a method of psicose by using the enzyme or transformed GRAS microorganism.

DISCLOSURE

Technical Problem

An embodiment provides a promoter being capable of producing psicose at high yield with high stability.

Another embodiment provides a regulating sequence being capable of regulating expression of Psicose epimerase in *Corynebacterium* sp. and containing the promoter.

A further embodiment provides a gene expression cassette including a nucleotide sequence encoding the psicose epimerase and the promoter or the regulating sequence.

A still further embodiment provides a vector being used in *Corynebacterium* sp., including a gene expression cassette including a nucleotide sequence encoding the psicose epimerase and the promoter or the regulating sequence.

Still another embodiment provides a *Corynebacterium* sp. cell expressing the psicose epimerase, including the gene expression cassette or being transformed by the gene expression cassette.

Still another embodiment provides a composition for the production of psicose, comprising at least one selected from the group consisting of Psicose epimerase, a recombinant cell, a culture of the recombinant cell, a lysate of the recombinant cell and an extract of culture.

Yet another embodiment provides a method of producing psicose, using at least one selected from the group consisting of Psicose epimerase, a recombinant cell, a culture of the recombinant cell, a lysate of the recombinant cell and an extract of culture.

Technical Solution

The present invention relates to a gene expression cassette capable of producing psicose at high yield with high stability, a GRAS (Generally recognized as safe) microorganism, a method of producing the enzyme by using the GRAS microorganism, and a method of producing the psicose by using the GRAS microorganism and enzyme.

The promoter derived from *E. coli* shows a low activity in *Corynebacterium* sp., because the expression inducing factor has a low permeability, and the gene expression material does not exist in *Corynebacterium* sp. Therefore, the present invention can provide a promoter being suitable for expressing a Psicose epimerase in *Corynebacterium* sp.

The present invention provides a promoter being capable of producing psicose at high yield with high stability, a regulating sequence including the promoter, and a gene expression cassette including the regulating sequence, thereby producing psicose epimerase in *Corynebacterium* sp. at a high yield with high stability in a large amount. In addition, the present inventors provide a psicose epimerase which can be expressed at a high rate in combination with the promoter, and a nucleotide sequence encoding the psicose epimerase.

Herein, the term "promoter", "nucleotide molecule having a promoter activity" or "promoter sequence" means a nucleotide molecule being capable of regulating the transcription or the expression of a nucleotide of interest, with being operably connected to the nucleotide of interest. The promoter can include a transcription promoter and expression promoter.

The nucleotide sequence of interest may not be linked to the promoter chemically, and can be linked to the promoter by using additional gene regulating sequence and/or linker nucleotide sequence, and the like. Preferably, the nucleotide sequence of interest to be transcribed can be located at a downstream of promoter (i.e., 3'-end of promoter sequence). The interval between the promoter sequence and the nucleotide sequence to be transcribed can be preferably 200 base pairs or less, or more preferably 100 bp or less.

Herein, the term "ribosome binding site" (RBS) or "Shine-Dalgano sequence" means a region of A/G rich polynucleotide sequence which is bound by a ribosome for translation.

Herein, the term "regulating sequence" means a nucleotide molecule having a regulating activity of gene expression such as transcription and/or translation of target polynucleotide and being operably linked to the target polynucleotide. The regulating sequence may be called as "regulating nucleotide sequence."

Hereinafter, the term "expression cassette" includes a regulating sequence being operably linked to the target nucleotide sequence, such as a nucleotide sequence coding the Psicose epimerase. Therefore, the expression cassette may include a nucleotide sequence required for expressing a protein after the transcription or the translation, as well as a nucleotide sequence regulating the transcription or the translation.

In the present invention, the nucleotide molecule is preferably a non-naturally occurring molecule, an isolated molecule or, a synthetic or recombinant type. The term, "isolated" nucleotide molecule may not include other nucleotide molecule in natural source, other cellular material or any component of culture medium in case of the recombination production method, or other chemical precursor or other chemicals in case of the chemical synthesis method.

In an embodiment, the regulating sequence used for *Corynebacterium* sp. can express the psicose epimerase having a high stability and enzyme activity in GRAS microorganism at a high yield and stability.

The present invention is described in detail hereinafter.

An embodiment of present invention provides a regulating sequence being operated in *Corynebacterium* sp. and thus a psicose epimerase having a high stability and activity can expressed in GRAS microorganism.

Another embodiment provides a gene expression cassette, producing a psicose epimerase in *Corynebacterium* sp., and comprising a nucleotide sequence encoding the psicose epimerase; and a regulating sequence being operably connected to the nucleotide sequence in the upstream and regulating the expression of the nucleotide sequence in *Corynebacterium* sp, wherein the regulating sequence comprising a promoter including a nucleotide sequence of SEQ ID NO: 1.

The regulating sequence includes a nucleotide sequence encoding the psicose epimerase; and a promoter expressing the psicose epimerase in GRAS microorganism, for example *Corynebacterium* sp. or a regulating sequence including the promoter. The regulating sequence can be an unmodified or modified nucleotide sequence which regulate the expression of nucleotide sequence encoding the Psicose epimerase in *Corynebacterium* sp.

The promoter includes a nucleotide molecule of SEQ ID NO: 1 and functional variants thereof. In an embodiment, the functional variant of promoter, shows at least 90% nucleotide sequence identity, for examples, at least 99%, 98%, 97%, 96%, 95%, 94%, 93%, 92%, 91%, or 90%.

The gene expression cassette or the regulating sequence further comprises at least one sequence selected from the group consisting of a ribosome binding site (RBS) sequence, a spacer sequence and a linker sequence.

The ribosome binding site sequence can be included at least one or more copy, for examples 1 to 5 copies, or 2 copies in the regulating sequence.

The regulating sequence may include a first RBS sequence and a first spacer sequence; a first RBS sequence, a first spacer sequence and a second RBS sequence which is connected to 3'-end of the first spacer directly or via a linker; and a first spacer sequence and a second RBS sequence which is connected to 3'-end of the first spacer directly or via a linker; and a second spacer.

Specifically, the regulating sequence includes one copy of RBS sequence. For example the regulating sequence includes a promoter of SEQ ID NO: 1, a first RBS sequence of SEQ ID NO: 2 and a first spacer selected from the group consisting of the sequences of SEQ ID NO: 3 to SEQ ID NO: 6 (promoter-RBS1-Spacer1). Optionally, the regulating sequence further includes a linker sequence in size of 1 to 100 bp which is connected to 3' end of the first spacer (promoter-RBS1-Spacer1-linker).

The regulating sequence includes two copies of RBS sequence. For example the regulating sequence includes (i) a promoter of SEQ ID NO: 1, and further includes at least one selected from the group consisting of (ii) a first RBS sequence of SEQ ID NO: 2, (iii) a first spacer selected from the group consisting of the sequences of SEQ ID NO: 3 to SEQ ID NO: 6, (iv) a linker sequence of SEQ ID NO: 12, and (v) a second spacer selected from the group consisting of the sequences of SEQ ID NO: 7 to 11. For examples, the second RBS sequence may be connected to 3'-end of the first spacer directly or via a linker (promoter-RBS1-Spacer1-RBS2, or promoter-RBS1-Spacer1-linker-RBS2). In the regulating sequence including two copies of RBS sequence, a second spacer can be connected to 3'-end of the second RBS sequence. In addition, the combination of first RBA and first spacer, or second RBS and second spacer can be repeated at least one or more, for examples 1 to 5 times, 2 times, 3 times, 4 times or 5 times.

The specific examples of unmodified regulating sequence are shown in the following.

(1) a promoter and a combination of RBS and space sequence which are linked to 3'-end of the promoter directly or via a linker (e.g., promoter-linker-RBS1-Spacer1, or promoter-RBS1-Spacer1), (2) a promoter and at least two combinations of RBS and space sequence (e.g., promoter-RBS1-Spacer1-RBS2-Spacer2), and (3) a promoter, at least two combinations of RBS and space sequence, and a linker which is located between the first spacer sequence and the second RBS (e.g., promoter-RBS1-Spacer1-linker sequence-RBS2-Spacer2).

In an embodiment, the ribosome binding site sequence is a nucleotide sequence in a size of 7 to 20 bp which including a nucleotide sequence of SEQ ID NO: 2, for example a nucleotide sequence of SEQ ID NO: 2.

The linker sequence is a nucleotide sequence in a size of 5 to 100 bp, or 5 to 80 bp, for example a nucleotide sequence of SEQ ID NO: 12.

The spacer sequence in the regulating sequence may be in the length of 3 to 15 bases of various bases, and increase the expression efficiency of gene located in downstream of the regulating sequence. The spacer sequence can be prepared in various base composition and base length by considering the gene of interest, the kind of host cell, and the like.

The modified regulating sequence of the present invention includes at least one base which substitutes at least one base of at least one selected from a first spacer and a second spacer.

For example, when the modified regulating sequence includes one copy of RBS, the modified regulating sequence includes promoter, first RBS and first spacer of which TT of a first base and a second base can be substituted with GA, GT or GC base.

When the modified regulating sequence includes two copies of RBS, TT of a first base and a second base of the first spacer connected to 3'-end of the first RBS can be substituted with GA, GT or GC; TT of a first base and a second base of the second spacer connected to 3'-end of the second RBS can be substituted with GG, GA, GT or GC; or TT of a first base and a second base of the first spacer can be substituted with GA, GT or GC and TT of a first base and a second base of the second spacer can be substituted with GG, GA, GT or GC.

For example, the first spacer sequence can be at least a nucleotide sequence selected from the group consisting of nucleotides of SEQ ID NO: 3 to 6. The second spacer sequence can be at least a nucleotide sequence selected from the group consisting of nucleotides of SEQ ID NO: 7 to 11.

In an embodiment, the promoter sequence, the RBS sequence, the first spacer and the second spacer, and their modified sequence, and the liker being applicable to the regulating sequence are exemplified in Table 1.

TABLE 1

| Seq ID No | sequence(5' -> 3') | name |
| --- | --- | --- |
| 1 | aagcgcctcatcagcggtaaccatcacgggttcgggtgcgaaaaaccatgcca taacaggaatgttcctttcgaaaattgaggaagccttatgcccttcaacccctactta gctgccaattattccgggcttgtgacccgctacccgataaataggtcggctgaaa aatttcgttgcaatatcaacaaaaaggcctatcattgggaggtgtcgcaccaagt acttttgcgaagcgccatctgacggattttcaaaagatgtatatgctcggtgcgga aacctac | promoter |
| 2 | gaaagga | RBS |
| 3 | ttttttaccc | 1$^{ST}$ SPACER R1TT |
| 4 | gattttaccc | 1$^{ST}$ SPACER R1GA |
| 5 | gttttaccc | 1$^{ST}$ SPACER R1GT |
| 6 | gcttttaccc | 1$^{ST}$ SPACER R1GC |
| 7 | ttacaaa | 2nd SPACER R2TT |
| 8 | gaacaaa | 2nd SPACER R2GA |
| 9 | gtacaaa | 2nd SPACER R2GT |
| 10 | gcacaaa | 2nd SPACER R2GC |
| 11 | ggacaaa | 2nd SPACER R2GG |
| 12 | atggctgtatacgaactcccagaactcgactacgcatacgac | linker |

The regulating sequence includes at least a polynucleotide selected from the group consisting of the sequences shown in SEQ ID NO: 13 to SEQ ID NO: 32, and regulates the expression of psciose epimerase in *Corynebacterium* sp.

The regulating sequence of the present invention can regulate the expression of psicose epimerase connected to the regulating sequence in the downstream in *Corynebacterium* sp. Therefore, the gene expression cassette of the

TABLE 2

| SEQ ID NO | sequence(5' -> 3') | name |
|---|---|---|
| 13 | (SEQ ID NO: 1) + gaaagga tttttaccc | RBS1/1st SPACER-TT |
| 14 | (SEQ ID NO: 1) + gaaagga gattttaccc | RBS1/1st SPACER-GA |
| 15 | (SEQ ID NO: 1) + gaaagga gttttaccc | RBS1/1st SPACER-GT |
| 16 | (번호1) + gaaagga gcttttaccc | RBS1/1st SPACER-GC |
| 17 | (SEQ ID NO: 1) + gaaagga tttttaccc atggctgtatacgaactcccagaactcgactacgcatacgac | RBS1/1st SPACER-TT linker |
| 18 | (SEQ ID NO: 1) + gaaagga gattttaccc atggctgtatacgaactcccagaactcgactacgcatacgac gaaagga ttacaaa | SOD-R1GA/R2TT |
| 19 | (SEQ ID NO: 1) + gaaagga gattttaccc atggctgtatacgaactcccagaactcgactacgcatacgac gaaagga gaacaaa | SOD-R1GA/R2GA |
| 20 | (SEQ ID NO: 1) + gaaagga gattttaccc atggctgtatacgaactcccagaactcgactacgcatacgac gaaagga gtacaaa | SOD-R1GA/R2GT |
| 21 | (SEQ ID NO: 1) + gaaagga gattttaccc atggctgtatacgaactcccagaactcgactacgcatacgac gaaagga gcacaaa | SOD-R1GA/R2GC |
| 22 | (SEQ ID NO: 1) + gaaagga gattttaccc atggctgtatacgaactcccagaactcgactacgcatacgac gaaagga ggacaaa | SOD-R1GA/R2GG |
| 23 | (SEQ ID NO: 1) + gaaagga gttttaccc atggctgtatacgaactcccagaactcgactacgcatacgac gaaagga ttacaaa | SOD-R1GT/R2TT |
| 24 | (SEQ ID NO: 1) + gaaagga gttttaccc atggctgtatacgaactcccagaactcgactacgcatacgac gaaagga gaacaaa | SOD-R1GT/R2GA |
| 25 | (SEQ ID NO: 1) + gaaagga gttttaccc atggctgtatacgaactcccagaactcgactacgcatacgac gaaagga gtacaaa | SOD-R1GT/R2GT |
| 26 | (SEQ ID NO: 1) + gaaagga gttttaccc atggctgtatacgaactcccagaactcgactacgcatacgac gaaagga gcacaaa | SOD-R1GT/R2GC |
| 27 | (SEQ ID NO: 1) + gaaagga gttttaccc atggctgtatacgaactcccagaactcgactacgcatacgac gaaagga ggacaaa | SOD-R1GT/R2GG |
| 28 | (SEQ ID NO: 1) + gaaagga gcttttaccc atggctgtatacgaactcccagaactcgactacgcatacgac gaaagga ttacaaa | SOD-R1GC/R2TT |
| 29 | (SEQ ID NO: 1) + gaaagga gcttttaccc atggctgtatacgaactcccagaactcgactacgcatacgac gaaagga gaacaaa | SOD-R1GC/R2GA |
| 30 | (SEQ ID NO: 1 + gaaagga gcttttaccc atggctgtatacgaactcccagaactcgactacgcatacgac gaaagga gtacaaa | SOD-R1GC/R2GT |
| 31 | (SEQ ID NO: 1) + gaaagga gcttttaccc atggctg tatacgaact cccagaactc gactacgcat acgac gaaagga gcacaaa | SOD-R1GC/R2GC |
| 32 | (SEQ ID NO: 1) + gaaagga gcttttaccc atggctg tatacgaact cccagaactc gactacgcat acgac gaaagga ggacaaa | SOD-R1GC/R2GG | present invention can be used for expressing the target gene in *Corynebacterium* sp., and the target gene can be a nucleotide sequence encoding psicose epimerase. The psicose epimerase can be derived from *Clostridiun scidens, Treponema primitia*, or *Ensifer adhaerens*. The psicose epimerase derived from *Agrobacterium tumefaciens* has a low enzyme activity and heat stability, and thus is not preferably.

The promoter derived from *E. coli* shows a low activity in *Corynebacterium* sp., because the expression inducing factor has a low permeability, and the gene expression material does not exist in *Corynebacterium* sp. Even though the same promoter is used, the promoter expression activity can be varied depending on the target gene to be expressed. The promoter being applicable to *Corynebacterium* sp. shows low promoter activity and *Corynebacterium* sp. dose not provide a wide choice of promoter. Therefore, the promoter being suitable for *Corynebacterium* sp. cannot be prepared easily. Although the promoter is suitably used in *Corynebacterium* sp., the promoter may have different regulating acidity of transcription or expression depending on the kind of target gene. The promoter, the regulating sequence and the gene expression cassette of present invention are very preferably used for expressing psciose epimerase in *Corynebacterium* sp.

The coding sequence of target protein may be connected to 3'-end of the regulating sequence used in *Corynebacterium* sp. directly or via a linker.

The psicose epimerase having a high enzyme activity and heat stability is preferably used. It is important to combine the promoter or the regulating sequence with the coding sequence of psicose epimerase. The coding sequence of psicose epimerase can provide a preferable expression level of protein, when it is used with the promoter of present invention, and a high heat stability can be obtained due to the good protein folding. The coding sequence of psicose epimerase according to the present invention is preferable to be used together with the promoter or the regulating sequence of the present invention.

In an embodiment, the psicose epimerase is derived from *Clostridiun scidens, Treponema primitia, Ensifer adhaerens* or *Ruminococcus torques*, and preferably at least an amino acid sequence shown in SEQ ID NO: 33 to 36.

As long as the psicose epimerase maintains the enzyme activity of converting fructose to psicose, any modified sequence of amino acid sequence shown in SEQ ID NO: 33 to 36 can be used by obtaining substitution, insertion and/or deletion of the partial amino acid. For example, the modified sequence can include an amino acid sequence having an amino acid sequence identify of 70% or higher, 80% or higher, 90% or higher, 95% or higher, or 는 99% or higher, compared to the amino acid sequence shown in SEQ ID NO: 33 to 36.

The coding sequence of psicose epimerase can be a nucleotide sequence of psicose epimerase derived from *Clostridiun scidens, Treponema primitia, Ensifer adhaerens* or *Ruminococcus torques*, or a modified sequenced obtained by optimizing the coding sequence to be suitable for expression in *E. coli* or *Corynebacterium* sp.

For example, the nucleotide sequence encoding the psicose epimerase can be a coding sequence of any one amino acid sequence selected from the sequences of SEQ ID NO: 33 to 36. Specifically, the nucleotide sequence can be any one selected from the sequences of SEQ ID NO: 37 to SEQ ID NO: 44, or a nucleotide sequence having substantially the same sequence homology to them. The term, substantially the same sequence homology means that any nucleotide sequence have the nucleotide sequence identity of 70% or higher, 90% or higher, or 98% or higher, compared to at least a nucleotide sequence selected from SEQ ID NO: 37 to SEQ ID NO: 44, when any nucleotide sequence is aligned with the nucleotide sequence selected from the sequences of SEQ ID NO: 37 to SEQ ID NO: 44 and is performed to sequence analysis.

In an embodiment, the psicose epimerase derived from *Clostridiun scidens* (CDPE) includes an amino acid sequence of SEQ ID NO: 33, and a nucleotide sequence encoding the amino acid sequence of SEQ ID NO: 33, for example the nucleotide sequence of SEQ ID NO: 37 or SEQ ID NO: 38

In an embodiment, the psicose epimerase derived from *Treponema primitia* (TDPE) includes an amino acid sequence of SEQ ID NO: 34, and a nucleotide sequence encoding the amino acid sequence of SEQ ID NO: 34, for example the nucleotide sequence of SEQ ID NO: 39 or SEQ ID NO: 40.

In an embodiment, the psicose epimerase derived from *Ensifer adhaerens* (EDPE) includes an amino acid sequence of SEQ ID NO: 35, and a nucleotide sequence encoding the amino acid sequence of SEQ ID NO: 35, for example the nucleotide sequence of SEQ ID NO: 41 or SEQ ID NO: 42.

In an embodiment, the psicose epimerase derived from *Ruminococcus torques* (RDPE) includes an amino acid sequence of SEQ ID NO: 36, and a nucleotide sequence encoding the amino acid sequence of SEQ ID NO: 36, for example the nucleotide sequence of SEQ ID NO: 43 or SEQ ID NO: 44.

The gene expression cassette of the present invention may comprise further at least a sequence selected from the group consisting of a replication origin, leader sequence, a selection marker, a cloning site, and a restriction enzyme recognition site.

In another embodiment, the gene expression cassette useful for *Corynebacterium* sp. comprising a promoter used for *Corynebacterium* sp., a regulating sequence including the promoter, or the regulating sequence and a polynucleotide encoding the psicose epimerase, *Corynebacterium* sp. expression cassette is provided.

The promoter used for *Corynebacterium* sp., the regulating sequence and the psicose epimerase are described in the above.

The gene expression cassette of the present invention may comprise further at least a sequence selected from the group consisting of a replication origin, leader sequence, a selection marker, a cloning site, and a restriction enzyme recognition site.

The gene expression cassette may be used in a naked polynucleotide construct, or in a recombinant vector. The term, a recombinant vector means a nucleotide molecule being capable of transferring a target polynucleotide which is operably linked to the recombinant vector. The target polynucleotide can be operably connected to a transcription regulator such as the promoter and a transcription terminator.

The recombinant vector can be a cloning vector or an expression vector according to the method known widely in the art (Francois Baneyx, current Opinion Biotechnology 1999, 10:411-421). The recombinant vector may be any vector which has been used for genetic recombination, and be any one selected from plasmid vector and viral vector (e.g., replication-deficient retrovirus, adenovirus and adeno-virus associated virus) 및 viral vector having an equivalent activity to the vector. The examples of recombinant vectors include at least a vector selected from the group consisting of pET, pKK223-3, pTrc99a, pKD, pXMJ19, pCES208 vector, and the like. Preferably, the vector may be *E. coli-Corynebacterium* shuttle vector (pCES208, J. Microbiol. Biotechnol., 18:639-647, 2008).

Accordingly, the vector including the gene expression cassette can be an expression vector such as a plasmid which can grow in *Corynebacterium* sp. and express the target protein.

The transcription terminator can be rrnB, rrnB_T1, rrnB_T2, or T7 terminator, or preferably T7 terminator derived from pET21a vector.

In an embodiment, a vector includes a promoter having a nucleotide sequence shown in SEQ ID NO: 1, or only a regulating sequence without the target gene. The vector can be a shuttle vector, a replication vector or an expression vector which can grow in *E. coli* and *Corynebacterium* sp.

In particular, the present invention provides a vector such as a plasmid including a regulating sequence to regulating the expression target polynucleotide sequence with being located in the upstream of target polynucleotide sequence. The regulating sequence may include a promoter having a nucleotide sequence of SEQ ID NO: 1, a first ribosome binding site (RBS) sequence and a first spacer sequence.

The regulating sequence may include a promoter, a first RBS sequence, a first spacer sequence, and a second RBS sequence connected to 3'-end of the first spacer directly or via a linker. The regulating sequence includes a promoter, a first RBS sequence, a first spacer sequence, a second RBS sequence and a second spacer sequence connected to 3'-end of the second RBS directly or via a linker.

In the vector including the promoter, the first spacer sequence comprises a modified nucleotide sequence where first base and second base (TT) in the nucleotide sequence of SEQ ID NO: 3 are substituted with GA, GT or GC. The modified first spacer can include a sequence of SEQ ID NO: 4, 5, or 6.

When the vector includes the first spacer and the second spacer, either or both of the first spacer and the second spacer can include at least a modified base. For example, the first spacer sequence includes a unmodified nucleotide sequence of SEQ ID NO: 3, but the second spacer sequence includes a modified nucleotide sequence where first and second base in the nucleotide sequence of SEQ ID NO:7 are substituted with GA, GT, GC or GG. The modified nucleotide sequence of second spacer may include a nucleotide sequence selected from the sequences of SEQ ID NO: 8 to 11.

Alternatively, the first and second base (TT) of the first spacer sequence having a nucleotide sequence of SEQ ID NO: 3 may be substituted with GA, GT or GC, and, the first and second base (TT) of the second spacer sequence having a nucleotide sequence of SEQ ID NO: 7 may be TT, GA, GT, GC or GG. The examples of first spacer sequences are a nucleotide sequence of SEQ ID NO: 4 to 6 and the examples of second spacer sequence are a nucleotide sequence of SEQ ID NO: 7 to 11.

In the vector including only a regulating sequence without a target gene, the expression cassette and the vector including the expression cassette including RBS, linker, first spacer, second spacer, a coding sequence of psicose epimerase and a regulating sequence are the same as described in the above.

In an embodiment, a recombinant *Corynebacterium* sp. cell including the gene expression cassette or transformed by the expression cassette can be provided.

The method of transforming a host cell by the recombinant vector can be performed by any transforming method which has been known to an ordinarily-skilled person in the art without limitation. For example, illustrative, non-limiting examples of the method include protoplast fusion, electroporation, projectile bombardment, and infection with a viral vector.

The transformed *Corynebacterium* sp. of present invention shows a high stability and expression efficiency of introduced psicose epimerase, and thus can maintains the high conversion rate of psicose for a long time. The transformed *Corynebacterium* sp. can be applied usefully to the production of psicose and increase the production yield of psicose.

Preferred *Corynebacterium* sp. may be *Corynebacterium glutamicum*, *Corynebacterium acetoglutamicum*, *Corynebacterium acetoacidophilum*, *Corynebacterium thermoaminogenes*, *Corynebacterium melassecola* or *Corynebacterium efficiens*.

The transformed *Corynebacterium* sp. of present invention may be a recombinant *Corynebacterium glutamicum*.

The culture of *Corynebacterium* sp. can be performed in the suitable medium according to the known method in the art. The culturing of the recombinant cell may be conducted under a medium and condition readily selected according to the property of the strain (host cell) by those skilled in the art. For example, the culturing may be a continuous-type culture, a semi-continuous-type culture, or a batch-type culture, but is not limited thereto. The culture medium being applicable to the present invention includes carbon source, nitrogen source, inorganic salts, vitamin and/or trace element. The preferred carbon sources include saccharide such as monosaccharide, disaccharide or polysaccharide. To maintain the metal ion concentration, the chelating agent can be added to the culture medium. All components of culture medium can be sterilized by heating at 1.5 bar and 121° C. for 20 minutes, or sterilization filtering.

In an embodiment, a composition for production of psicose including at least one selected from the group consisting of an psicose epimerase obtained by using the recombinant *Corynebacterium* sp., a recombinant cell, a culture of the recombinant cell, a lysate of the recombinant cell and an extract of cell culture can be provided.

In another embodiment, a method for producing psicose including a step of reacting fructose-containing substrate with a composition for production of psicose including at least one selected from the group consisting of an psicose epimerase obtained by using the recombinant *Corynebacterium* sp., a recombinant cell, a culture of the recombinant cell, a lysate of the recombinant cell and an extract of cell culture or cell lysate can be provided.

The culture can contains an enzyme protein produced from the recombinant *Corynebacterium* sp cell, and may include the recombinant cell, or may alternatively be in a cell-free form. The lysate may result from the lysis of the recombinant cell or may include a supernatant obtained by centrifuging the lysate, so that it contains the enzymatic protein produced from the recombinant cell in n either case. Unless stated otherwise herein, the recombinant cell means at least one selected from the group consisting of a cell mass of the strain, a culture of the strain and a lysate of the strain.

The method of producing psicose includes a step of reacting the *Corynebacterium* sp. with fructose-containing substrate. In one embodiment, the reaction between the enzymatic proteins and fructose may be carried out by culturing a cell mass of the recombinant cell in a medium containing fructose. The reaction of the *Corynebacterium* sp. with fructose-containing substrate can be carried out by contacting the *Corynebacterium* sp. with fructose which can be the contact of fructose with at least one selected from the group consisting of a cell mass of the strain, a culture of the strain and a lysate of the strain. In addition, the reaction of the *Corynebacterium* sp. with fructose-containing substrate can be carried out by mixing the *Corynebacterium* sp. with fructose, or by contacting the *Corynebacterium* sp. immobilized in the substrate with fructose, so as to converting fructose to psicose.

For effective production of psicose in the method, fructose, serving as a substrate, is used at a concentration of 40 to 75% (w/v) in the reaction mixture, for example, at a concentration of 50 to 75% (w/v). A lower concentration than the lower limit of fructose may decrease the economic feasibility of psicose in this manner. On the other hand, if present at a concentration higher than the upper limit, fructose is less apt to dissolve. Hence, the concentration preferably falls within the range. Fructose may be in the form of a solution in a buffer or water (e.g., distilled water).

The reaction may be carried out at a pH of 6 to 9.5, for example, at a pH of 7 to 9, at a pH of 7 to 8, at a pH of 8 to 9. the reaction may be conducted under the temperature condition of 40° C. or higher, for example, 4° C. or higher. When the reaction may be conducted at a temperature of 80° C., the substrate fructose may be apt to undergo browning. Hence, the reaction may be conducted under the temperature condition of from 40 to 80° C., for example 50 to 75° C., 60 to 75° C., or 68 to 75° C.

In addition, a longer period of reaction time leads to a higher conversion rate of psicose. It is recommended to conduct the reaction for 1 hr or longer, for example, 2 hrs or longer, 3 hrs or longer, 4 hrs or longer, 5 hrs or longer, or 6 hrs or longer. However, the reaction time is preferably set forth within 48 hrs since when the reaction time is extended over 48 hrs, the increment of the conversion rate of psicose becomes slight, or may be decreased. Hence, the reaction time may be set forth to range from 1 to 48 hrs, from 2 to 48 hrs, from 3 to 48 hrs, from 4 to 48 hrs, from 5 to 48 hrs, or from 6 to 48 hrs. In consideration of industrial and economic aspects, the reaction time may fall within the range of 1 to 48 hrs, 2 to 36 hrs, 3 to 24 hrs, 3 to 12 hrs, or 3 to 6 hrs, but is not be limited thereto. This condition is selected in order to maximize the conversion yield from fructose to psicose.

In addition, when the recombinant cell is used in the psicose-producing method, its concentration may be set forth to range from 5 mg (dcw: dry cell weight)/ml or higher in the entire reaction mixture, for example, range from 5 to 100 mg (dcw)/ml, from 10 to 90 mg (dcw)/ml, from 20 to 80 mg (dcw)/ml, from 30 to 70 mg (dcw)/ml, from 40 to 60 mg (dcw)/ml, or from 45 to 55 mg (dcw)/ml. If the concentration of cell mass is below the lower limit, poor or almost no conversion activity of psicose is exhibited. On the other hand, a concentration exceeding the upper limit means crowding of cells which are likely to act as an obstructer to the optimization of the entire conversion yield of psicose.

The enzymatic protein having psicose conversion activity (for example psicose epimerase) may show the property of a metalloenzyme the activity of which is controlled by metal ions. Hence, the presence of a metal ion may promote the reaction catalyzed by the enzymatic protein, thus increasing the production yield of psicose.

Therefore, the composition for the production of psicose may further comprise a metal ion. the method for producing psicose may further comprise adding a metal ion. In one embodiment, the metal ion may be added to the culture medium in the process of culture, or may be added during the culturing process.

In another embodiment, the metal ion may be added to fructose or a mixture of fructose and *Corynebacterium* sp. The metal ion can be added to a support to which the enzymatic proteins are immobilized (before the addition of D-fructose) or to a mixture of an enzymatic protein-immobilized support and D-fructose (after the addition of D-fructose), or may be added in mixture with D-fructose or individually together with D-fructose.

The metal ion which can contribute to an improvement in the production yield of psicose may be selected from the group consisting of a copper ion, a manganese ion, a calcium ion, a magnesium ion, a zinc ion, a nickel ion, a cobalt ion, an iron ion, an aluminum ion, and any combination thereof. For example, either or both of a manganese ion and a cobalt ion may be used. In consideration of an improvement in the production yield of psicose, the metal ion can be added at an amount of 0.5 mM or more. when the amount of the metal ion exceeds 5 mM, the effect of addition is insignificant compared to the surplus amount. So, the amount of the metal ion is set forth to be 5 mM or less. For example, the metal ion is used in an amount of 0.5 mM to 5 mM, for example 0.5 mM to 2 mM.

So long as it establishes an environment for maintaining the activity of the strain or the enzymatic protein produced from the strain for a long period of time, any support configured to immobilize the strain or the enzymatic protein thereto may be used. For example, sodium alginate may serve as the support. Sodium alginate, a naturally occurring colloidal polysaccharide abundantly found in the cell walls of brown algae, consists of β-D-mannuronic acid and α-L-gluronic acid, with a covalent β 1-4 linkage therebetween. Allowing for the stable immobilization of the strain or the enzyme thereto, the linear polymer may be advantageous for the production yield of psicose.

In one embodiment, a 1.5~4.0% (w/v) sodium alginate solution (e.g., aqueous sodium alginate solution), for example, an about 2.5% (w/v) sodium alginate solution may be used for immobilizing the strain. By way of example, a cell mass of the strain, a culture broth containing the enzyme produced by the strain, or a lysate of the strain is mixed with 1 to 2 volumes of an aqueous sodium alginate solution, and the mixture is dripped to a 0.2 M calcium ion solution using a syringe pump and a vacuum pump, to form beads to which the cell mass of the strain, the culture containing the enzyme produced by the strain, or the lysate of the strain are immobilized. The enzyme may be purified from the strain, a culture of the strain or a lysate of the strain using a typical method, for instance, dialysis, precipitation, adsorption, electrophoresis, affinity chromatography, or ion exchange chromatography.

The psicose-producing method comprises the reaction of the enzymatic proteins with D-fructose. In one embodiment, the reaction between the enzymatic proteins and D-fructose may be carried out by contacting the enzymatic proteins with D-fructose.

In one embodiment, the reaction between the enzymatic proteins and fructose may be carried out by contacting the enzymatic proteins with fructose. In another embodiment, the contact between the enzymatic proteins and fructose may be carried out by, for example, mixing the enzymatic proteins with fructose or bringing fructose into contact with the enzymatic proteins immobilized to a support. In a further embodiment, the reaction between the enzymatic proteins and fructose may be carried out by culturing a cell mass of the recombinant cell in a medium containing fructose. The reaction of the enzymatic proteins with fructose leads to conversion and thus production of psicose from D-fructose.

In the psicose-producing method, efficiency may be brought in the production of psicose when the enzymatic proteins are used at a concentration of 0.001 mg/ml to 1.0 mg/ml in the reaction mixture, at a concentration of 0.005 mg/ml to 1.0 mg/ml, at a concentration of 0.01 mg/ml to 1.0 mg/ml, at a concentration of 0.01 mg/ml to 0.1 mg/ml, or at a concentration of 0.05 mg/ml to 0.1 mg/ml. When the enzymatic proteins are used at a concentration lower than the lower limit, the conversion yield of psicose may be poor. On the other hand, too high a concentration of the enzymatic proteins decreases the industrial economy of psicose production.

For effective production of psicose in the method, fructose, serving as a substrate, is used at a concentration of 40 to 75% (w/v) in the reaction mixture, for example, at a concentration of 50 to 75% (w/v). A lower concentration than the lower limit of fructose may decrease the economic feasibility of psicose in this manner. On the other hand, if present at a concentration higher than the upper limit, fructose is less apt to dissolve. Hence, the concentration preferably falls within the range. Fructose may be in the form of a solution in a buffer or water (e.g., distilled water).

By considering the optimal reaction condition of enzyme protein, the reaction pH, temperature and the enzyme concentration can be adjusted. For example, the reaction pH can be 6 to 9, or the temperature can be 30° C. or higher, for example 40° C. or higher, because the fructose may be apt to undergo browning at 80° C. or higher. In addition, a longer period of reaction time leads to a higher conversion rate of psicose. It is recommended to conduct the reaction for 1 hr or longer, because of the heat-stability of enzyme (at 50° C.). When the reaction time exceeds 8 hours, it cannot have any significant effect on the conversion rate of psicose or can decrease the conversion rate. Thus, the reaction time is preferable 8 hours or shorter than.

When the recombinant cell is used in the psicose-producing method, its concentration may be set forth to range from 5 mg (dcw: dry cell weight)/ml or higher in the entire reaction mixture.

In an embodiment, the method for producing psicose may comprise a step of reacting the fructose with a recombinant cell expressing psicose epimerase or the psicose epimerase separated from the recombinant cell. In one embodiment, the method for producing psicose may comprise culturing and recovering a recombinant cell.

After being produced from fructose using the method of the present invention, psicose can be purified by a typical method which can be readily selected by a person skilled in the art, for example, from the group consisting of centrifugation, filtration, crystallization, ion exchange chromatography, and a combination.

Advantageous Effects

A gene expression system which expressing the psicose epimerase in a large amount with GRAS microorganism such as *Corynebacterium* sp., a vector and *Corynebacterium* sp. are provided according to the present invention, and the psicose epimerase obtained by using the gene expression system can produce psicose form the fructose-containing substrate.

BRIEF DESCRIPTION OF DRAWINGS

The file of this patent contains at least one drawing executed in color. Copies of this patent with color drawing(s) will be provided by the Patent and Trademark Office upon request and payment of the necessary fee.

FIG. 1 is a cleavage map of a recombinant vector for expressing psicose 3-epimerase protein according to one embodiment of the present invention.

FIG. 2 is a picture showing the protein amount by using SDS-PAGE of lysate of *Corynebacterium* sp. cell cultured by using bead beater.

MODE FOR INVENTION

A better understanding of the present invention may be obtained through the following examples which are set forth to illustrate, but are not to be construed as the limit of the present invention.

Example 1. Plasmid Production

Example 1-1: Vector Production with Sod Promoter

The nucleotide sequence (CDPE gene; Genbank: EDS06411.1) encoding psicose epimerase derived from *Clostridiuim scindens* ATCC 35704 was optimized for *E. coli* to produce a modified nucleotide sequence which was called as CDPE. The optimized polynucleotide (SEQ ID NO: 36), sod regulating sequence (SEQ ID NO: 17: sod promoter-RBS-SPACER R1TT-LINKER) derived from *Corynebacterium* gDNA, and T7 terminator of pET21a vector were amplified by PCR method to produce each template and were ligated to one template according to the overlapping PCR method. The one template was cloned into pGEM T-easy vector according to T-vector cloning method and was analyzed for the sequence. Specifically, the polynucleotide included the sod regulating sequence of SEQ ID NO: 17, the optimized CDPE coding sequence for *E. coli* of SEQ ID NO: 36, and T7-terminator.

The whole polynucleotide was inserted into the same restriction recognition site of pCES208 (J. Microbiol. Biotechnol., 18:639-647, 2008) with restriction enzyme NotI and XbaI (NEB), to produce the recombinant vector of pCES208/psicose epimerase (pCES_sodCDPE). The cleavage map of recombinant vector (pCES_sodCDPE) is shown in FIG. 1.

Example 1-2: Vector Production with Saturation Mutagenesis

In order to prepare a vector using the saturation mutagenesis, the primers including -NN- as a target site were prepared. Specifically, TT in the 3'-end of first RBS (GAAGGA) and the second RBS were decided as target site and asked Genotec to synthesize the primer. The primer sequences, saturation mutagenesis site, and primer binding site were summarized in Table 2.

TABLE 2

| Primer name | sequence (5' -> 3') | SEQ ID NO |
|---|---|---|
| RBS1_F | GGTGCGGAAACCTACGAAAGGANNTTTTACCCATGGCTGTATACGAAC | 45 |
| RBS1_R | GTTCGTATACAGCCATGGGTAAAANNTCCTTTCGTAGGTTTCCGCACC | 46 |
| RBS2_F | GACTACGCATACGACGAAAGGANNACAAAATGAAACACGGTATCTACTAC | 47 |
| RBS2_R | GTAGTAGATACCGTGTTTCATTTTGTNNTCCTTTCGTCGTATGCGTAGTC | 48 |

The front fragment and the rear fragment divided by a reference site of -NN- were obtained by PCR, to produce one template produced according to the overlapping PCR method. The template was inserted into pCES208 plasmid by ligating with XbaI and NotI site, so as to obtain the plasmid according to the Saturation mutagenesis.

Example 2. Transformation and Screening Transformed E. coli

Example 2-1: E. coli Transformation

E. coli DH10b strain was transformed with the plasmid obtained in EXAMPLE 1 by electrophoresis and screened. Specifically, kanamycin was poured to 1.5 ml tube to be 15 μg/ml of the final concentration of kanamycin, and add with 1 ml of LB (tryptone 10 mg/L, NaCl 10 mg/L, yeast extract 5 mg/L). The randomly-selected colonies were inoculated on the plate and cultured at 37° C. for about 16 hours. Then, the cell was harvested to remove the culture medium, was reacted with 50% fructose (substrate) dissolved in 50 mM PIPES buffer (pH 7.0) by the addition of 1 mM $Mn^{2+}$ at 60° C. for 30 minutes, and quenched at 100° C. for 5 minutes.

Example 2-2: Screening with Psicose Conversion Rate

The product of EXAMPLE 2-1 was analyzed with LC analysis to compare the conversion rate of psicose with that of pCES_sodCDPE. Then, the transformant with modified gene having a higher conversion rate was selected. Specifically, the conversion rate was obtained by analyzing the LC peak of substrate (fructose) and product (psicose) and the peak area.

The comparison of LC peak area confirmed that the decreasing extent of psicose production and substrate consumption. The standard curves were obtained by preparing the samples with different fructose concentrations of 10, 20, 50, 100, 120, 150 mM and the samples with different psicose concentration of 1, 2, 5, 10, 20, 50 mM to be $R^2$ of 0.99 or higher. Then, each formula was inferred from the standard curves, and the fructose concentration and psicose concentration were obtained by using the LC peak area.

The final values were indicated as psicose conversion rate which was proportional to the amount of expressed CDPE. Thus, as the amount of produced psicose increase, the amount of expressed CDPE increases.

As a result, 6 mutants including three mutants at R1 site and 3 mutants at R2 site were selected and designated as name R1-1, R1-4, R1-8, R2-1, R2-5, or R2-11. Compared to the LC analysis result of the control including unmodified sequence (pCES_sod CDPE), four mutants were selected based on the psicose conversion rate and shown in Table 3.

TABLE 3

| Sample | Psicose conversion rate (%) |
|---|---|
| sod_CDPE | 5.15 |
| R1-1 | 8.59 |
| R1-4 | 8.94 |
| R2-5 | 5.66 |
| R2-11 | 6.07 |

As shown in Table 3, finally-selected mutants showing increased conversion rate of psicose were R1-1 and R1-4 at R1 site and R2-5 and R2-11 at R2 site, and thus, 4 mutants showed increased CDPE expression.

Example 2-3: Identification of Modified Sequence

On the basis of nucleotide sequence of SEQ ID NO: 3 in the unmodified pCES_sodCDPE, R1-1 had GA substituted and R1-4 had GG substituted at TT of control target site.

On the basis of nucleotide sequence of SEQ ID NO: 7 in the non-mutated pCES_sodCDPE, R2-5 and R2-11 had GG substituted at TT of control target site.

Example 3. Measurement of CDPE Expression Rate in Corynebacterium

Corynebacterium glutaricum was transformed with the plasmid obtained in EXAMPLE 1 by electrophoresis. The colony was inoculated on LB medium (tryptone 10 g/L, NaCl 10 g/L, yeast extract 5 g/L) enriched with Kanamycin to be final concentration of Kanamycin as 15 μg/ml, and cultured at 30° C. and 250 rpm for 16 hours. Then, 1 mL of culture solution was inoculated in 100 ml LB medium containing 15 μg/ml of Kanamycin and then cultured at 30° C. and 250 rpm for 16 hours.

The recombinant Corynebacterium glutaricum transformed with the plasmid obtained in EXAMPLE 1-1 (pCES_sodCDPE) was deposited on Oct. 29, 2014, at the Korea Culture Center of Microorganisms (KCCM) located at 25 Hongjenae-2ga-gil, Seodaemun-gu, Seoul, Republic of Korea, as Accession number of KCCM11593P.

In addition, Corynebacterium glutaricum was transformed with 4 mutants obtained in EXAMPLE 2 respectively and obtained by culturing them in 100 mL of LB medium. The cells were lysed and purified by using His-tag purification method. Then, the cell lysate was carried out with SDS-PAGE to identify the conversion rate of CDPE.

Specifically, the cultured cells were lysed with Bead beater and the supernatant was collected, mixed with sample buffer at 1:1 and heated at 100° C. for 5 minutes. The prepared sample was analyzed with electrophoresis by suing 12% SDS-PAGE gel (composition: running gel—3.3 ml $H_2O$, 4.0 ml 30% acrylamide, 2.5 ml 1.5M Tris buffer (pH 8.8), 100 µl 10% SDS, 100 µl, 10% APS, 4 µl TEMED/ stacking gel—1.4 ml $H_2O$, 0.33 ml 30% acrylamide, 0.25 ml 1.0 M Tris buffer (pH 6.8), 20 µl 10% SDS, 20 µl 10% APS, 2 µl TEMED) at 180 V for 50 minutes to identify the protein expression.

After identifying the CDPE expression on SDS-PAGE gel, the product was purified according to His-Tag purification method using Ni-NTA resin, and the conversion rate of psicose was calculated by using the formula of conversion rate (%)=(Purified protein (mg)/Total soluble protein (mg))* 100). The calculated conversion rate was indicated in Table 4.

In following Table 4, the whole cellular proteins means all proteins inside the cell expressing cell psicose epimerase, and the amount of psicose epimerase is referred to an amount of purified psicose epimerase. Therefore, the conversion rate means the calculated value showing a ratio of expressed target protein to the whole cellular proteins.

TABLE 4

| sample | CDPE conversion rate (%) |
|---|---|
| Sod_CDPE | 10 |
| R1-1 | 15 |
| R1-4 | 9.5 |
| R2-5 | 8.3 |
| R2-11 | 8.5 |

As shown in Table 4, the concentration of purified CDEP of R1-1 showed about 1.5 times as high as the transformant with recombinant vector (pCES_sodCDPE). On the other hand, other samples showed a low conversion rate.

Example 4. Psicose Production by Using Enzyme Reaction

*Corynebacterium glutaricum* was transformed with 4 mutants of R1-1, R1-4, R2-5, and R2-11 obtained in EXAMPLE 2 respectively and obtained by culturing them in 100 mL of LB medium. The unpurified crude enzyme was used for converting 50 mM fructose-containing substrate to psicose. Then, the amount of produced psicose was analyzed.

The mutant cells expressing CDPE were broken. The supernatant including the protein was obtained, measured to be 0.007 mg/ml of the concentration of whole cellular protein, and added to the substrate containing 50 mM fructose added by 1 mM $Mn^{2+}$. Then, the reaction was carried out at pH 7.0 PIPES 50 mM and 60° C. for 5, 10, or 15 minutes, and then quenched with heating at 100° C. for 5 minutes.

The conversion rate of psicose was compared by LC analysis. Specifically, the conversion rate was obtained by analyzing the LC peak of substrate (fructose) and product (psicose) and the peak area.

The LC analysis was performed by using Refractive Index Detector (Agilent 1260 RID) of HPLC (Agilent, USA) equipped with Aminex HPX-87C column (BIO-RAD), water with the temperature of 80° C. as a mobile phase, and the column speed of 0.6 ml/min. Then, the conversion rate of psicose was calculated on the basis of the formula of conversion rate by using the amount of produced psicose and unconsumed fructose measured from the LC peak. The calculated values are shown in Table 5.

Conversion rate (%)=Amount of produced psicose (g/l)/(amount of produced psicose+amount of remaining fructose) (g/l)*100     [Formula]

TABLE 5

| Sample | Psicose conversion rate (%) at reaction for 5 minutes |
|---|---|
| Sod-CDPE | 15.66 |
| R1-1 | 17.24 |
| R1-4 | 14.39 |
| R2-5 | 14.10 |
| R2-11 | 13.65 |

As shown in Table 5, the conversion rate of R1-1 was higher than sod-CDPEII. Other modified sequence showed a somewhat reduction of conversion rate, compared to sod-CDPE.

Example 5. Psicose Production by Using *Corynebacterium* Cell Reaction

*Corynebacterium glutaricum* was transformed with 4 mutants of R1-1, R1-4, R2-5, and R2-11 obtained in EXAMPLE 2 respectively and obtained by culturing them in 100 mL of LB medium. The substrate containing 50 wt % of fructose was reacted by using the cell reaction and the conversion rate was compared.

Specifically, The 0.5 to 2 mg/ml of mutant cells expressing CDPE were added to the substrate containing fructose at solid content of 50 wt % and 1 mM $Mn^{2+}$, reacted at pH 7.0 PIPES 50 mM and 60° C. and quenched by heating at 100° C. for 5 minutes.

The conversion reaction was performed by using each mutant cell and the conversion rate was calculated according to the LC analysis method. the LC analysis was performed by using Refractive Index Detector (Agilent 1260 RID) of HPLC (Agilent, USA) equipped with Aminex HPX-87C column (BIO-RAD), water with the temperature of 80° C. as a mobile phase, and the column speed of 0.6 ml/min. Then, the conversion rate of psicose was calculated on the basis of the formula of conversion rate by using the amount of produced psicose and unconsumed fructose measured from the LC peak. The calculated values are shown in Table 6.

Conversion rate (%)=amount of produced psicose (g/l)/(amount of produced psicose+amount of unconsumed fructose) (g/l)*100     [Formula]

TABLE 6

| Sample | Psicose conversion rate (%) |
|---|---|
| Sod-CDPEII | 6.02 |
| R1-1 | 8.34 |
| R1-4 | 5.99 |
| R2-5 | 4.79 |
| R2-11 | 5.29 |

As shown in Table 6, the conversion rate of mutant R1-1 was higher than sod-CDPEII. Other modified sequence showed a somewhat reduction of conversion rate, compared to sod-CDPE.

Example 6: Comparison of Heat Stability in *Corynebacterium* Cell Reaction

Besides the high conversion rate of the cell, the cell converting the psicose epimerase stably is also important in the industrial field. Therefore, this experiment was carried out to confirm the heat stability of the cell.

In order to confirm the heat stability of cell at 50° C., 1.0 mg/ml of cells pre-treated with surfactant was re-suspended in 50 mM PIPES buffer (pH 7.0) and heated at 50° C. The cell was sampled at each heating hour and was used for the conversion reaction that the sampled cell was added to substrate containing 50% fructose and 1 mM of $Mn^{2+}$ and reacted at 50° C. for 60 minutes.

The psicose conversion rate and the decreased extent of sampled cells were shown in Table 7, by referencing zero of conversion rate and zero of heating time.

TABLE 7

| Reaction Minutes | psicose conversion rate (%) of pCES_sodCDPE | Relative heat stability of pCES_sodCDPE | psicose conversion rate (%) of R1-1 | Relative heat stability of R1-1 |
|---|---|---|---|---|
| 0 | 8.4 | 100 | 11.62 | 100 |
| 120 | 7.5 | 89.21 | 10.77 | 92.7 |
| 240 | 7.27 | 86.56 | 9.56 | 82.27 |
| 360 | 7.02 | 83.52 | 9.03 | 77.74 |
| 540 | 6.81 | 81.05 | 9.19 | 79.1 |
| 840 | 6.54 | 77.88 | 8.9 | 76.6 |
| 1020 | 6.52 | 77.65 | 8.4 | 72.31 |
| 1200 | 6.15 | 73.17 | 7.32 | 62.98 |
| 1320 | 5.94 | 70.64 | 8.04 | 69.24 |
| 1560 | 5.92 | 70.42 | 8.15 | 70.14 |
| 1680 | 5.71 | 67.92 | 7.75 | 66.75 |
| 1740 | 5.24 | 62.32 | 6.82 | 58.73 |

As shown in Table 7, the heat stability of R-1 was not different from pCES_sodCDPE and thus R1-1 mutant had good heat stability. The half-life of R1-1 was expected to be about 1800 minutes.

Example 7: Production of Modified Regulating Sequence and CDPE Expression

Example 7-1: Vector Production Including a Modified Regulating Sequence

TT in the 3'-end of first RBS (GAAGGA) and the second RBS were decided as target site and asked Genotec to synthesize the -NN-primer in order to substitute TT with GT, GC, or GG. The primer sequences, saturation mutagenesis site, and primer binding site were summarized in Table 8.

TABLE 8

| Primer | sequence (5'->3') | Seq ID No |
|---|---|---|
| RBS1GT_F | GGTGCGGAAACCTACGAAAGGAGTTTTTACCCATGGCTGTATACGAAC | 49 |
| RBS1GT_R | GTTCGTATACAGCCATGGGTAAAAACTCCTTTCGTAGGTTTCCGCACC | 50 |
| RBS1GC_F | GGTGCGGAAACCTACGAAAGGAGCTTTTACCCATGGCTGTATACGAAC | 51 |
| RBS1GC_R | GTTCGTATACAGCCATGGGTAAAAGCTCCTTTCGTAGGTTTCCGCACC | 52 |
| RBS1GG_F | GGTGCGGAAACCTACGAAAGGAGGTTTTACCCATGGCTGTATACGAAC | 53 |
| RBS1GG_R | GTTCGTATACAGCCATGGGTAAAACCTCCTTTCGTAGGTTTCCGCACC | 54 |

The front fragment and the rear fragment divided by a reference site of -NN- were obtained by PCR, to produce one template produced according to the overlapping PCR method. The template was inserted into pCES208 plasmid by ligating with XbaI and NotI site, so as to obtain the plasmid according to the Saturation mutagenesis.

Example 7-2: Measurement of CDPE Expression Rate

*Corynebacterium glutaricum* was transformed with the plasmid including the mutated sequence obtained in EXAMPLE 7-2, cultured in 100 ml of LB medium, and lysed and purified according to the His-tag purification method using Ni-NTA resin. The concentration of whole cellular protein and the purified protein (CDPE) were measured according to Bradford assay and the conversion rate of target protein was calculated.

Specifically, the cultured cells were lysed with Bead beater and the supernatant was collected, mixed with sample buffer at 1:1 and heated at 100° C. for 5 minutes. The prepared sample was analyzed with electrophoresis by suing 12% SDS-PAGE gel (composition: running gel—3.3 ml $H_2O$, 4.0 ml 30% acrylamide, 2.5 ml 1.5M Tris buffer (pH 8.8), 100 µl 10% SDS, 100 µl, 10% APS, 4 µl TEMED/ stacking gel—1.4 ml $H_2O$, 0.33 ml 30% acrylamide, 0.25 ml 1.0 M Tris buffer (pH 6.8), 20 µl 10% SDS, 20 µl 10% APS, 2 µl TEMED) at 180 V for 50 minutes to identify the protein expression. FIG. 2 shows a picture showing the protein amount by using SDS-PAGE of lysate of *Corynebacterium* sp. cell cultured by using bead beater.

After identifying the CDPE expression on SDS-PAGE gel, the product was purified according to His-Tag purification method using Ni-NTA resin, and the conversion rate of psicose was calculated by using the formula of conversion rate (%)=(Purified protein (mg)/Total soluble protein (mg))* 100). The calculated conversion rate was indicated in Table 9.

TABLE 9

| plasmid | Whole cellular protein(mg) | psicose epimerase enzyme (mg) | conversion rate (%) |
|---|---|---|---|
| pCES_sodCII | 10.7 | 1.1 | 10.3 |
| R1GA | 11.5 | 1.7 | 14.8 |
| R1GT | 10.9 | 1.6 | 14.7 |

TABLE 9-continued

| plasmid | Whole cellular protein(mg) | psicose epimerase enzyme (mg) | conversion rate (%) |
|---|---|---|---|
| R1GC | 8.2 | 0.8 | 9.8 |
| R1GG | 10.8 | 0.7 | 6.5 |

As shown in Table 9, the conversion rates of R1GA and R1GT were higher than pCES_sodCDPE. R1GC shows similar enzyme activity and R1GG showed decreased enzyme activity.

Example 7-3: Psicose Production with Cellular Reaction

According to the substantially same method of EXAMPLE 5, *Corynebacterium* strain was transformed with mutants respectively, cultured in 100 ml of LB medium, and add to the psicose conversion reaction to compare the psicose conversion rate. The result was shown in Table 10.

TABLE 10

| sample | psicose conversion rate (%) | Relative conversion rate (%) |
|---|---|---|
| R1GG | 4.58 | 100 |
| R1TT | 6.73 | 147 |
| R1GA | 9.76 | 213 |
| R1GT | 9.17 | 200 |
| R1GC | 7.39 | 161 |

As shown in Table 10, by referencing 100 of psicose conversion rate of R1GG, the relative conversion rate of R1GA was 213, R1GT was 200, and R1GC was 161, and R1TT was 147. Therefore, all mutant showed increased conversion rate.

7-4: Comparison of Heat Stability in Cell Reaction

Besides the high conversion rate of the cell, the cell converting the psicose epimerase stably is also important in the industrial field. Therefore, this experiment was carried out to confirm the heat stability of the cell.

In order to confirm the heat stability of cell at 50° C., 1.0 mg/ml of cells pre-treated with surfactant was re-suspended in 50 mM PIPES buffer (pH 7.0) and heated at 50° C. The cell was sampled at each heating hour and was used for the conversion reaction that the sampled cell was added to substrate containing 50% fructose and 1 mM of $Mn^{2+}$ and reacted at 50° C. for 60 minutes.

The psicose conversion rate and the decreased extent of sampled cells were shown in Table 11, by referencing zero of conversion rate and zero of heating time.

TABLE 11

| Reaction minutes | pCES_sodCII | R1GA | R1GT | R1GC | R1GG |
|---|---|---|---|---|---|
| 0 | 100 | 100 | 100 | 100 | 100 |
| 240 | 86.6 | 82.3 | 83.9 | 91 | 83.8 |
| 360 | 83.5 | 77.7 | 74.1 | 84.8 | 79.2 |
| 840 | 77.9 | 76.6 | 72.3 | 84.7 | 78.1 |
| 1200 | 73.2 | 75.8 | 73.2 | 81.9 | 64.2 |
| 1560 | 70.4 | 70.1 | 66.9 | 77.6 | 62.3 |
| 1680 | 67.9 | 66.7 | 65.2 | 73.8 | 56.1 |
| 1740 | 62.3 | 58.7 | 56.2 | 52.4 | 55.3 |

Example 8: Production of Modified Regulating Sequence and CDPE Expression

8-1: Vector Production Including a Modified Regulating Sequence

As a result of the modified sequence according to the Saturation mutagenesis, TT located in the first spacer after the first RBS affected the CDPE expression. Thus, TT located in the first spacer after the first RBS was substituted with GT, GC, or GG, tested for the CDPE expression and selected as R1-1(GA substituted for TT after the first RBS). The nucleotide sequence of R1-1 was used as a template for substituting TT after the second RBS with GA, GT, GC, or GG. The mutants were tested for the psicose conversion rate.

The double mutants were produced by using the mutant (R1-1) obtained in EXAMPLE 5 as a template and the following primer in Table 12.

TABLE 12

| Primer | Sequence (5'->3') | SEQ ID NO |
|---|---|---|
| RBS1GA/RBS2GA_F | GACTACGCATACGACGAAAGGAGAACAAAATGAAACACGGTATCTACTAC | 55 |
| RBS1GA/RBS2GA_R | GTAGTAGATACCGTGTTTCATTTTGTTCTCCTTTCGTCGTATGCGTAGTC | 56 |
| RBS1GA/RBS2GT_F | GACTACGCATACGACGAAAGGAGTACAAAATGAAACACGGTATCTACTAC | 57 |
| RBS1GA/RBS2GT_R | GTAGTAGATACCGTGTTTCATTTTGTACTCCTTTCGTCGTATGCGTAGTC | 58 |
| RBS1GA/RBS2GC_F | GACTACGCATACGACGAAAGGAGCACAAAATGAAACACGGTATCTACTAC | 59 |
| RBS1GA/RBS2GC_R | GTAGTAGATACCGTGTTTCATTTTGTGCTCCTTTCGTCGTATGCGTAGTC | 60 |
| RBS1GA/RBS2GG_F | GACTACGCATACGACGAAAGGAGGACAAAATGAAACACGGTATCTACTAC | 61 |

TABLE 12-continued

| Primer | Sequence (5'->3') | SEQ ID NO |
|---|---|---|
| RBS1GA/RBS2GG_R | GTAGTAGATACCGTGTTTCATTTTGTCCTCCTTTCGTCGTATGCGTAGTC | 62 |

8-2: Measurement of CDPE Expression Rate

According to the same method of EXAMPLE 7-2, *Corynebacterium glutaricum* was transformed with the plasmid including the modified regulating sequence. The CDPE conversion rate was determined and indicated in Table 13.

As shown in Table 13, the whole cellular proteins means all proteins inside the cell expressing cell psicose epimerase, and the amount of psicose epimerase is referred to an amount of purified psicose epimerase. Therefore, the conversion rate means the calculated value showing a ratio of expressed target protein to the whole cellular proteins.

TABLE 13

| microorganism | whole cellular protein (mg) | psicose epimerase enzyme (mg) | conversion rate (%) |
|---|---|---|---|
| pCES_sodCII | 10.7 | 1.1 | 10.3 |
| R1GA/R2GA | 10.3 | 1.5 | 14.5 |
| R1GA/R2GT | 10.7 | 1.6 | 15.0 |
| R1GA/R2GC | 12.8 | 1.8 | 14.1 |
| R1GA/R2GG | 11.9 | 1.7 | 14.3 |

As shown in Table 13, the double mutations of R1GA/R2GA, R1GA/R2GT, R1GA/R2GC and R1GA/R2GG showed an increased conversion rate of CDPE than pCES_sodCDPE.

8-3: Psicose Production by Using Cellular Reaction

According to the same method of EXAMPLE 8-2, *Corynebacterium glutaricum* was transformed with the plasmid including the modified regulating sequence, and cultured in 100 ml of LB medium. The CDPE conversion rate was determined by the cellular reaction and indicated in Table 14.

To identify the product, the conversion rate was obtained by analyzing the LC peak of substrate (fructose) and product (psicose) and the peak area. As a result, the initial psicose production rate of cell (Unit/g-DCW) was analyzed by using on various surfactant solutions and indicated in Table 14.

The LC analysis was performed by using Refractive Index Detector (Agilent 1260 RID) of HPLC (Agilent, USA) equipped with Aminex HPX-87C column (BIO-RAD), water with the temperature of 80° C. as a mobile phase, and the column speed of 0.6 ml/min.

TABLE 14

| Sample | psicose conversion rate (%) | Relative conversion rate (%) |
|---|---|---|
| R1GG | 4.58 | 100 |
| R1GA/R2GC | 9.95 | 217 |

As shown in Table 14, the relative conversion rate (%) of double mutation R1GA/R2GC on showed 217, on the basis of 100 of psicose conversion rate of R1GG.

8-4: Comparison of Heat Stability in Cellular Reaction

Besides the high conversion rate of the cell, the cell converting the psicose epimerase stably is also important in the industrial field. Therefore, this experiment was carried out to confirm the heat stability of the cell.

In order to confirm the heat stability of cell at 50° C., 1.0 mg/ml of cells pre-treated with surfactant was re-suspended in 50 mM PIPES buffer (pH 7.0) and heated at 50° C. The cell was sampled at each heating hour and was used for the conversion reaction that the sampled cell was added to substrate containing 50% fructose and 1 mM of $Mn^{2+}$ and reacted at 50° C. for 60 minutes.

The psicose conversion rate and the decreased extent of sampled cells were shown in Table 15 by referencing zero of conversion rate and zero of heating time.

TABLE 15

| Reaction times (minutes) | pCES_sodCII | R1GA/R2GA | R1GA/R2GT | R1GA/R2GC | R1GA/R2GG |
|---|---|---|---|---|---|
| 0 | 100 | 100 | 100 | 100 | 100 |
| 240 | 86.6 | 86.9 | 90.8 | 90.4 | 88.5 |
| 360 | 83.5 | 90 | 81.5 | 92.2 | 83.6 |
| 840 | 77.9 | 80.9 | 68.4 | 77.4 | 82.4 |
| 1200 | 73.2 | 77.3 | 64.6 | 73.6 | 72.2 |
| 1560 | 70.4 | 74.1 | 62.7 | 70.8 | 75.4 |
| 1680 | 67.9 | 70.5 | 59.6 | 67.4 | 71.8 |
| 1740 | 62.3 | 66.4 | 56.9 | 61.7 | 63.2 |

As shown in Table 15, by comparing the heat stability of pCES_sodCDPE and double mutation, the heat stability of double mutation was not different from pCES_sodCDPE and thus the double mutant had good heat stability. Accordingly, the modified regulating sequence affect the expression of CDPE, but not influence the heat stability.

The invention claimed is:

1. A method of producing a psicose epimerase, comprising:

culturing a recombinant *Corynebacterium* sp. cell transformed by a vector comprising a gene expression cassette, and reacting a fructose-containing substrate with at least one selected from the group consisting of an psicose epimerase obtained from the culture of the recombinant *Corynebacterium* sp., a recombinant cell, a culture of the recombinant cell, a lysate of the recombinant cell and an extract of cell culture or the cell lysate, and wherein the gene expression cassette, producing a psicose epimerase in *Corynebacterium* sp., and comprising:

a nucleotide sequence encoding the psicose epimerase; and a regulating sequence being operably connected to the nucleotide sequence in the upstream regulating the expression of the nucleotide sequence in *Corynebac-*

*terium* sp., and comprising a promoter, a ribosome binding site (RBS) sequence and a first spacer sequence in the direction of 5' to 3', wherein the promoter includes the nucleotide sequence of SEQ ID NO: 1, the ribosome binding site (RBS) sequence is a nucleotide sequence in a size of 7 to 20 bases including the nucleotide sequence of SEQ ID NO: 2, and the first spacer sequence is selected from the group consisting of the nucleotide sequences of SEQ ID NO: 4 to SEQ ID NO: 6.

2. The method according to claim 1, wherein the reacting step is performed by contacting the fructose-containing substrate with a support immobilized by the psicose epimerase or the recombinant cell.

3. The method according to claim 1, wherein the method comprise further a step of adding at least a metal ion selected from the group consisting of a copper ion, a manganese ion, a calcium ion, a magnesium ion, a zinc ion, a nickel ion, a cobalt ion, an iron ion and an aluminum ion.

4. The method according to claim 1, wherein the fructose-containing substrate comprises a fructose at a concentration of 40 to 75 (w/w) %.

5. The method according to claim 1, wherein the method is performed under the condition of pH 6 to 9 and temperature of 40 to 80° C.

6. The method according to claim 1, wherein the regulating sequence further comprises a second RBS sequence which is connected to 3'-end of the first spacer directly or via a linker sequence in a length of 5 to 100 bases, and wherein the second RBS sequence is a nucleotide sequence in a size of 7 to 20 bases including the nucleotide sequence of SEQ ID NO: 2.

7. The method according to claim 6, wherein the linker sequence is a nucleotide sequence in a size of 42 to 100 bp which includes the nucleotide sequence of SEQ ID NO: 12.

8. The method according to claim 1, wherein the regulating sequence further comprises a second spacer sequence selected from the group consisting of the nucleotide sequences of SEQ ID NO: 7 to SEQ ID NO: 11, wherein the second spacer is connected to 3'-end of the second RBS.

9. The method according to claim 7, wherein the regulating sequence further comprises a second spacer sequence selected from the group consisting of the nucleotide sequences of SEQ ID NO: 7 to SEQ ID NO: 11, wherein the second spacer is connected to 3'-end of the second RBS.

10. The method according to claim 6, wherein the regulating sequence comprise a nucleotide sequence selected from the group consisting of the sequences of SEQ ID NO: 14 to SEQ ID NO: 16.

11. The method according to claim 7, wherein the regulating sequence comprise a nucleotide sequence selected from the group consisting of the sequences of SEQ ID NO: 14 to SEQ ID NO: 16, and the linker sequence of SEQ ID NO: 12.

12. The method according to claim 1, wherein the regulating sequence comprises the promoter nucleotide sequence of SEQ ID NO: 1,
the RBS nucleotide sequence of SEQ ID NO: 2,
the first spacer sequence selected from the group consisting of the sequences of SEQ ID NO: 4 to SEQ ID NO: 6; and
further comprises a second RBS nucleotide sequence of SEQ ID NO: 2, and a second spacer sequence selected from the group consisting of the sequences of SEQ ID NO: 7 to SEQ ID NO: 11.

13. The method according to claim 1, wherein the *Corynebacterium* sp. is at least one selected from the group consisting of *Corynebacterium glutamicum, Corynebacterium acetoglutamicum, Corynebacterium acetoacidophilum, Corynebacterium thermoaminogenes, Corynebacterium melassecola* and *Corynebacterium efficiens*.

14. The method according to claim 1, wherein the psicose epimerase is derived from *Clostridium scidens, Treponema primitia, Ensifer adhaerens* or *Ruminococcus torques*.

15. The method according to claim 14, wherein the psicose epimerase is an amino acid sequence selected from the group consisting of nucleotides of SEQ ID NO: 33 to SEQ ID NO: 36.

16. The method according to claim 15, wherein the nucleotide sequence encoding the psicose epimerase is a nucleotide sequence selected from the group consisting of nucleotides of SEQ ID NO: 37 to SEQ ID NO: 44.

* * * * *